US010001437B2

(12) United States Patent
Lednev

(10) Patent No.: US 10,001,437 B2
(45) Date of Patent: Jun. 19, 2018

(54) SPECTROSCOPY FOR GUNSHOT RESIDUE ANALYSIS

(71) Applicant: THE RESEARCH FOUNDATION FOR THE STATE UNIVERSITY OF NEW YORK, Albany, NY (US)

(72) Inventor: Igor K. Lednev, Glenmont, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days. days.

(21) Appl. No.: 15/026,529

(22) PCT Filed: Sep. 26, 2014

(86) PCT No.: PCT/US2014/057802
§ 371 (c)(1),
(2) Date: Mar. 31, 2016

(87) PCT Pub. No.: WO2015/050791
PCT Pub. Date: Apr. 9, 2015

(65) Prior Publication Data
US 2016/0238522 A1    Aug. 18, 2016

Related U.S. Application Data

(60) Provisional application No. 61/887,059, filed on Oct. 4, 2013.

(51) Int. Cl.
*G01N 21/00* (2006.01)
*G01N 21/35* (2014.01)
(Continued)

(52) U.S. Cl.
CPC ............. *G01N 21/35* (2013.01); *F42B 5/00* (2013.01); *G01N 21/3586* (2013.01);
(Continued)

(58) Field of Classification Search
CPC .......... F42B 35/00; F42B 5/00; G01N 21/35; G01N 21/3586; G01N 21/552;
(Continued)

(56) References Cited

U.S. PATENT DOCUMENTS 5,760,898 A    6/1998  Haley et al.
7,499,808 B2   3/2009  Sinha
(Continued)

FOREIGN PATENT DOCUMENTS

WO    WO 2011103161 A2 *  8/2011  ............. F42B 35/00

OTHER PUBLICATIONS

"Ammunition Identification by Means of the Organic Analysis of Gunshot Residues Using Raman Spectroscopy", Anal. Chem. 84 (8): 3581-3585 (2012), American Chemical Society, by Maria López-López et al.*
(Continued)

*Primary Examiner* — Jamil Ahmed
(74) *Attorney, Agent, or Firm* — LeClairRyan PLLC

(57) ABSTRACT

The present invention relates to a method of detecting inorganic gunshot residue (GSR) particles. The method includes providing a sample comprising gunshot residue, subjecting the sample to spectroscopic analysis to produce a spectroscopic signature for the sample, and identifying inorganic gunshot residue particles based on the spectroscopic signature for the sample. Also disclosed is a method of detecting gunshot residue particles. The method includes providing a sample comprising gunshot residue, subjecting the sample to spectroscopic analysis to produce a spectroscopic signature for the sample, where the spectroscopic signature spans a range of wavenumbers, creating one or more spectroscopic maps from the spectroscopic signature for the sample, where each different spectroscopic map is for a different wavenumber, and identifying gunshot residue
(Continued)

particles based on the one or more spectroscopic maps for the sample.

28 Claims, 10 Drawing Sheets

(51) Int. Cl.
  *G01N 21/552*  (2014.01)
  *G01N 21/65*  (2006.01)
  *G01N 21/3586*  (2014.01)
  *F42B 5/00*  (2006.01)

(52) U.S. Cl.
  CPC ......... *G01N 21/552* (2013.01); *G01N 21/658* (2013.01); *G01N 2021/3595* (2013.01); *G01N 2021/653* (2013.01); *G01N 2201/06113* (2013.01)

(58) Field of Classification Search
  CPC ......... G01N 21/658; G01N 2021/3595; G01N 2021/653; G01N 2201/06113; G01N 21/64; G01N 27/447; G01N 23/223; H01J 37/27; G01T 1/36; G01J 3/44; G01J 3/42
  See application file for complete search history.

(56) References Cited

U.S. PATENT DOCUMENTS

2006/0126168 A1 6/2006 Treado et al.
2013/0043130 A1 2/2013 Lednev et al.

OTHER PUBLICATIONS

"Attenuated Total Reflectance-FT-IR Spectroscopy for Gunshot Residue Analysis: Potential for Ammunition Determination", Anal. Chem. 85 (15): 7287-7294 (2013), American Chemical Society, by Justin Bueno et al.*
"Raman Spectroscopic Analysis of Gunshot Residue Offering Great Potential for Caliber Differentiation", Anal. Chem. 84 (1): 4334-4339 (2012), American Chemical Society, by Justin Bueno et al.*
"Confocal Raman Microscopy Analysis of Multilayer Polymer Films", p. 1-4, (2008), Thermo Scientific, by Guillory et al.*
International Preliminary Report on Patentability for corresponding International Application No. PCT/US2014/057802 (dated Apr. 14, 2016).
Brettell et al., "Forensic Science," Analytical Chemistry 81(12):4695-4711 (2009).
Xu et al., "Deaths: Final Data for 2007," National Vital Statistics Reports 58(19):1-136 (2010).
Romolo and Margot, "Identification of Gunshot Residue: A Critical Review," Forensic Science International 119:195-211 (2001).
Meng and Caddy, "Gunshot Residue Analysis—A Review," J. Forensic Sciences 42(4):553-570 (1997).
Silva et al., "Gunshot Residues: Screening Analysis by Laser-Induced Breakdown Spectroscopy," J. Brazilian Chem. Soc. 20(10):1687-1694 (2009).
Garofano et al., "Gunshot Residue—Further Studies on Particles of Environmental and Occupational Origin," Forensic Sci. Int'l. 103(1):1-21 (1999).
Dockery and Goode, "Laser-Induced Breakdown Spectroscopy for the Detection of Gunshot Residues on the Hands of a Shooter," Applied Optics 42(30):6153-6158 (2003).
Santos et al., "Firing Distance Estimation Through the Analysis of the Gunshot Residue Deposit Pattern Around the Bullet Entrance Hole by Inductively Coupled Plasma—Mass Spectrometry—An Experimental Study," Am. J. Forensic Med. Pathol. 28(1 ):24-30 (2007).
Capannesi et al., "Determination of Firing Distance and Firing Angle by Neutron Activation Analysis in a Case Involving Gunshot Wounds," Forensic Sci. Int'l. 51(2-3):75-84 (1993).
Neri et al., "The Determination of Firing Distance Applying a Microscopic Quantitative Method and Confocal Laser Scanning Microscopy for Detection of Gunshot Residue Particles," Int'l. J. Legal Med. 121(4):287-292 (2007).
Brown et al., "Image Analysis of Gunshot Residue on Entry Wounds: II-A Statistical Estimation of Firing Range," Forensic Sci. Int'l. 100(3):179-186 (1999).
Burleson et al., "Forensic Analysis of a Single Particle of Partially Burnt Gunpowder by Solid Phase Micro-Extraction-Gas Chromatography-Nitrogen Phosphorus Detector," J. Chromatography A 1216(22): 4679-4683 (2009).
Nesbitt et al., "Detection of Gunshot Residue by Use of the Scanning Electron Microscope," J. Forensic Sci. 21 :595-610 (1976).
Steffen et al., "Chemometric Classification of Gunshot Residues Based on Energy Dispersive X-ray Microanalysis and Inductively Coupled Plasma Analysis With Mass-Spectrometric Detection," Spectrochimica Acta Part B 62 (9):1028-1036 (2007).
Wallace and McQuillan, "Discharge Residues from Cartridge-Operated Industrial Tools," J. Forensic Sci. Soc. 24(5):495-508 (1984).
Ali et al., "In-situ Detection of Single Particles of Explosive on Clothing with Confocal Raman Microscopy," Talanta 78(3):1201-1203 (2009).
Abbott et al., "Resonance Raman and UV-Visible Spectroscopy of Black Dyes on Textiles," Forensic Sci. Int'l. 202(1-3):54-63 (2010).
Hodges and Akhavan,"The Use of Fourier Transform Raman Spectroscopy in the Forensic Identification Illicit Drugs and Explosives," Spectrochimica Acta Part A 46A(2):303-307 (1990).
Ali et al., "In-situ Detection of Drugs-of-Abuse on Clothing Using Confocal Raman Microcsopy," Analytica Chimica Acta 615:63-72 (2008).
Virkler and Lednev, "Raman Spectroscopy Offers Great Potential for the Nondestructive Confirmatory Identification of Body Fluids," Forensic Sci. Int'l. 181:e1-e5 (2008).
Dalby et al., "Analysis of Gunshot Residue and Associated Materials—A Review," J. Forensic Sci. 55(4):924-943 (2010).
Pun and Gallusser, "Macroscopic Observation of the Morphological Characteristics of the Ammunition Gunpowder," Forensic Sci. Int'l. 175:179-185 (2008).
Sharma and Lahiri, "A Preliminary Investigation Into the Use of FTIR Microscopy as a Probe for the Identification of Bullet Entrance Holes and the Distance of Firing," Science & Justice 49:197-204 (2009).
Thissen et al., "Multivariate Calibration with Least-Squares Support Vector Machines," Anal. Chem. 76 (11):3099-3105 (2004).
Hargreaves et al., "Analysis of Seized Drugs Using Portable Raman Spectroscopy in an Airport Environment—a Proof of Principle Study," J. Raman Spectroscopy 39:873-880 (2008).
Rodger et al., "The In-Situ Analysis of Lipsticks by Surface Enhanced Resonance Raman Scattering," Analyst 123:1823-1826 (1998).
Suzuki et al., "In Situ Identification and Analysis of Automotive Paint Pigments Using Line Segment Excitation Raman Spectroscopy: 1. Inorganic Topcoat Pigments," J. Forensic Sci. 46: 1053-1069 (2001).
Mazzella et al., "Raman Sepctroscopy of Blue Gel Pen Inks,"Forensic Sci. Int. 152:241-247 (2005).
Grasselli et al., "Chemical Applications of Raman Spectroscopy," New York:John Wiley & Sons 2-4 (1981).
Yan et al., "Surface-Enhanced Raman Scattering Detection of Chemical and Biological Agents Using a Portable Raman Integrated Tunable Sensor," Sensors and Actuators B 121:61-66 (2007).
Eckenrode et al., "Portable Raman Spectroscopy Systems for Field Analysis," Forensic Science Communications 3:(2001).
Lednev, I. K., "Vibrational Spectroscopy: Biological Applications of Ultraviolet Raman Spectroscopy," in: V. N. Uvsersky, and E. A. Permyakov, Protein Structures, Methods in Protein Structures and Stability Analysis, Chapter 3.1:1-26 (2007).

(56) References Cited

OTHER PUBLICATIONS

Thomas et al., "Raman Spectroscopy and the Forensic Analysis of Black/Grey and Blue Cotton Fibers Part. 1: Investigation of the Effects of Varying Laser Wavelength,"Forensic Sci. Int. 152:189-197 (2005).
Franke, J. E. "Inverse Least Squares and Classical Least Squares Methods for Quantitative Vibrational Spectroscopy," In Chalmers, eds., Handbook of Vibrational Spectroscopy, vol. 3, New York:John Whiley & Sons, Ltd., pp. 2276-2292 (2001).
Schwoeble and Exline, "Current Methods in Forensic Gunshot Residue Analysis," CRC Press: New York 12-14, 19-20, 32-33, 42-43 (2000).
Sarkis et al., "Measurements of Gunshot Residues by Sector Field Inductively Coupled Plasma Mass Spectrometry—Further Studies With Pistols," Forensic Science International 172:63-66 (2007).
Malinowski, E. R., Factor Analysis in Chemistry, 3 Ed., New York: John Wiley & Sons, Inc. 17-18 (2002).
Skoog et al., Principles of Instrumental Analysis, 5th Edition. Saunders College Publishing 223-225 (1998).
Stich et al., "Raman Microscopic Identification of Gunshot Residues," J. Raman Spectroscopy 29:787-790 (1998).
Abraham et al., "Application of X-Ray Diffraction Techniques in Forensic Science," Forensic Science Communications 9(2) (2007).
Shashilov et al., "Advanced Statistical and Numerical Methods for Spectroscopic Characterization of Protein Structural Evolution," Chem Rev. 110:5692-5713 (2010).
Wise et al., "PLS Toolbox 3.5 for Use with Matlab.," vol. 17, Eigenvector Research Inc:Manson, Wash. 1-254 (2005).
Mark et al., "Chemometrics in Spectroscopy," Elsevier, 2-3 (2007).
Chau et al., "Chemometrics: From Basics to Wavelet Transformation," Hoboken, N.J.:John Wiley & Sons, Inc, 81-84 (2004).
International Search Report and Written Opinion for PCT/US2011/025048, dated Sep. 26, 2011, 11 pages.
Zeichner et al., "Application of lead isotope analysis in shooting incident investigations," Forensic Science International 158:52-64 (2005).
Bueno et al., "Raman Microspectroscopic Chemical Mapping and Chemometric Classification for the Identification of Gunshot Residue on Adhesive Tape." Anal. Bioanal. Chem. 406(19):4595-4599 (2014).
Bueno et al., "Attenuated Total Reflectance-FT-IR Imaging for Rapid and Automated Detection of Gunshot Residue," Anal Chem, 86(7): 3389-3396 (2014).
Bueno et al., "Advanced Statistical Analysis and Discrimination of Gunshot Residue Implementing Combined Raman and FTIR Data," Anal. Methods 5:6292-6296 (2013).

Leggett et al., "Gunshot Residue Analysis via Organic Stabilizers and Nitrocellulose," Microchemicals Journal 39:76-85 (1989).
Bueno et al., "Raman Spectroscopic Analysis of Gunshot Residue Offering Great Potential for Caliber Differentiation," Anal. Chem. 84(1):4334-4339 (2012).
Lopez-Lopez et al., "Ammunition Identification by Means of the Organic Analysis of Gunshot Residues Using Raman Spectroscopy," Anal. Chem. 84(8):3581-3585 (2012).
Bueno et al., "Attenuated Total Reflectance-FT-IR Spectroscopy for Gunshot Residue Analysis: Potential for Ammunition Determination," Anal. Chem. 85(15):7287-7294 (2013).
Guillory et al., "Confocal Raman Microscopy Analysis of Multilayer Polymer Films," Thermo Scientific (2008) <URL: http://www.revbase.com/tt/sl.achx?z+73090c66&dataid=250130&ft=1>.
Byrne, R., "Course Review—Manufacturing & Testing of PSA Tapes," (2012) <URL: www.gatewayanalytical.com/blog/course-review-manufacturing-testing-of-psa-tapes/>.
PCT International Search Report and Written Opinion corresponding to PCT/US2014/057802, filed Sep. 26, 2014 (dated Dec. 29, 2014).
Office Action for U.S. Appl. No. 13/578,925 dated Nov. 24, 2015.
Office Action for U.S. Appl. No. 13/578,925 dated Apr. 7, 2015.
Vandenabeele et al., "Micro-Raman Spectroscopy of Natural and Synthetic Indigo Samples," Analyst 128:187-193 (2003).
Ricci et al., "Enhancing Forensic Science with Spectroscopic Imaging," Proc. of SPIE vol. 6402, 10 pp. (2006).
Ng et al., "Detection of Illicit Substances in Fingerprints by Infrared Spectral Imaging," Anal. Bioanal. Chem. 394:2039-2048 (2009).
Hamasha et al., "Sensitive and Specific Discrimination of Pathogenic and Nonpathogenic *Escherichia coli* using Raman Spectroscopy—A Comparison to Two Multivariate Analysis Techniques," Biomedical Optics Express 4 (4):461-469 (2013).
Li et al., "Noninvasive Liver Diseases Detection Based on Serum Surface Enhanced Raman Spectroscopy and Statistical Analysis," Optics Express 23(14):18361-18372 (2015).
Meisel et al., "Raman Spectroscopy as a Potential Tool for Detection of *Brucella* spp. in Milk," Applied and Environmental Microbiology 78(16):5575-5583 (2012).
Croft, S., The Analysis of Unfired Propellant Particles by Gas Chromatography—Mass Spectrometry: A Forensic Approach, School of Physical and Chemical Sciences, Queensland University of Technology, Masters of Applied Science Thesis, 96 pp. (Apr. 2008).
Jarvis et al., "Genetic Algorithm Optimization for Pre-Processing and Variable Selection of Spectrosopic Data," Bioinformatics 21(7):860-868 (2005).

\* cited by examiner

SPECTROSCOPY FOR GUNSHOT RESIDUE ANALYSIS

This application is a national stage application under 35 U.S.C. § 371 of PCT Application No. PCT/US2014/057802, filed Sep. 25, 2014, which claims the priority benefit of U.S. Provisional Patent Application Ser. No. 61/887,059, filed Oct. 4, 2013, the disclosure of which is hereby incorporated by reference in its entirety.

FIELD OF THE INVENTION

The present invention relates to spectroscopy for gunshot residue analysis.

BACKGROUND OF THE INVENTION

Gunshot residue (GSR) particles represent the burnt and partially burnt chemical remains of ammunition expelled from a firearm discharge. GSR possesses evidentiary value which can assist investigators in shooting incident reconstruction (Haag, *Shooting Incident Reconstruction;* Elsevier: Amsterdam, (2006)). Organic GSR (OGSR) is composed primarily of explosive materials originating from the propellant of the discharged ammunition, while inorganic gunshot residue (IGSR) is formed from contributions of the ammunition propellant, primer, projectile (bullet), and cartridge case (Dalby et al., *J. Forensic Sci.* 55:924 (2010)). Detection of GSR at a crime scene is critical, as it is indicative of a shooting incident. Furthermore, detection of GSR on the body or clothing of a person indicates their presence, and often degree of involvement, in a crime (Cetó et al., *Anal. Chem.* 84:10306 (2012)).

Recovery, detection, and preservation of these discharge samples is often challenging. Crime scene recovery of GSR can be achieved through several collection methods, including adhesive tapes, glues, liquid swabbing, and vacuum apparatuses (Dalby et al., *J. Forensic Sci.* 55:924 (2010)). Tape collection, or "tape lifting", has been established as the most widely accepted and efficient technique for GSR collecting from different surfaces (Degaetano et al., *J. Forensic Sci.* 35:1087 (1990)). Tape collection is performed by the pressing of double-sided pressure sensitive adhesive (PSA) tape against a surface of interest that contains GSR. These surfaces include the clothing, skin, and hair of a suspect or victim, as well as any surfaces adjacent to the firearm discharge (Romolo et al., *Forensic Sci. Int'l* 119:195 (2001); Zeichner et al., *J. Forensic Sci.* 38:571 (1993); Shaffer at al., *Scanning* 21:99 (1999); Wrobel et al., *J. Forensic Sci.* 43:178 (1998)).

Scanning electron microscopy combined with energy dispersive X-ray spectroscopy (SEM/EDS) is the most widely accepted technique for GSR detection (ASTM; American Society for Testing and Materials (2010)). SEM/EDS specializes in the detection of the heavy metals; lead, barium, and antimony, where the presence of all three is considered characteristic to IGSR (Nesbitt et al., *J. Forensic Sci.* 21:595 (1976)). SEM/EDS analysis has been applied to IGSR detection on several collection substrates. Specialized tape substrates coated with a conductive carbon material are required for SEM analysis. Unfortunately, the collection of debris and fibers from certain surfaces, is known to inhibit SEM analysis of tape collection substrates, as these analytes are not electronically conductive (Mastruko, *Forensic Sci. Int'l* 136 (Suppl. 1):153 (2003)). Other pitfalls for the technique include relatively expensive instrumentation and time consuming analyses (Romolo et al., *Forensic Sci. Int'l* 119:195 (2001)). The most rapid SEM/EDS approach was found to take over 8 hours to scan an 12.5 mm² area for detecting GSR originating from a specific ammunition (Lebiedzik et al., *J. Forensic Sci.* 45:83 (2000)). A threshold for the number of "characteristic" IGSR particles must be achieved before GSR detection can be confirmed. However, the advent of heavy metal free (HMF) ammunition reduces the probability of detecting "characteristic" IGSR particles and weakens the specificity (rate of true negatives) of the technique for the identification of GSR. GSR particles originating from HMF ammunition are devoid of Pb, Ba, and Sb, and are susceptible to higher rates of misclassification (false negatives, etc.) via SEM/EDS detection (ASTM; American Society for Testing and Materials (2010); Martiny et al., *Forensic Sci. Int'l* 177:E9 (2008); Garofano et al., *Forensic Sci. Int'l* 103:1 (1999); Cardinetti et al., *Forensic Sci. Int'l* 143:1 (2004)). Other elemental analyses, such as laser ablation inductively coupled mass spectrometry (LA-ICPMS), have attempted to reproduce the high-throughput analysis of GSR on tape offered by SEM/EDS (Abrego et al., *Anal. Chem.* 84:2402 (2012)). Although, LA-ICPMS was reported to be capable of analyzing a 12.8 mm² area in approximately 66 minutes, it unfortunately required expensive instrumentation and was also dependent upon detection of heavy metals. Additionally, the laser spot diameter of 160 µm provided bulk analysis, eliminating the possibility of detecting individual GSR particles.

Vibrational spectroscopy (IR and Raman) represents an ideal approach for GSR analysis, due to its non-destructive and selective nature. Advanced statistical analysis was used to differentiate Raman spectroscopic data collected from GSR particles originating from different firearm-ammunition combinations (Bueno et al., *Anal. Chem.* 84:4334. (2012)). Raman spectroscopic analysis of smokeless ammunition propellant and its subsequent GSR was also investigated. Specific chemical additives from the discharged ammunition identified in the resulting GSR, were used as a predictive tool for ammunition identification (López-López et al., *Anal. Chem.* 84:3581 (2012)). Previous macroscopic ATR-FT-IR investigation into GSR analysis has targeted the differentiation of non-equivalent GSR samples from ATR-FT-IR data (Bueno et al., *Anal. Chem.* 85:7287 (2013)) and combined Raman spectroscopic and ATR-FT-IR data (Bueno et al., *Anal. Methods* (2013)). Shooting distance estimations based on GSR analysis were performed via macroscopic ATR-FT-IR analysis (Mou et al., *J. of Forensic Sci.* 53:1381 (2008)) and traditional FT-IR spectroscopy utilizing KBr pellets (Sharma et al., *Science & Justice,* 49:197 (2009)). Traditional FT-IR spectroscopy was also previously implemented to characterize organic gunshot residue (OGSR) (Leggett et al., *Microchemical Journal* 39:76 (1989)). However, these methods have been limited to chemical characterization of GSR.

The present invention is directed to overcoming these and other deficiencies in the art.

SUMMARY OF THE INVENTION

One aspect of the present invention relates to a method of detecting inorganic gunshot residue (GSR) particles. The method includes providing a sample comprising gunshot residue, subjecting the sample to spectroscopic analysis to produce a spectroscopic signature for the sample, and identifying inorganic gunshot residue particles based on the spectroscopic signature for the sample.

A second aspect of the present invention relates to a method of detecting gunshot residue particles. The method includes providing a sample comprising gunshot residue, subjecting the sample to spectroscopic analysis to produce a spectroscopic signature for the sample, wherein the spectroscopic signature spans a range of wavenumbers, creating one or more spectroscopic maps from the spectroscopic signature for the sample, where each different spectroscopic map is for a different wavenumber, and identifying gunshot residue particles based on the one or more spectroscopic maps for the sample.

A spectroscopic method of detecting inorganic gunshot residue particles provides several improvements over current elemental analyses used for GSR detection. This method is more labor, time and cost effective. Furthermore, the method of the present invention will allow for more sensitive detection of inorganic gunshot residue particles. Additionally, detection of explosive particles (2,4-DNT) will be useful in the fields of home land security and counter-terrorism.

A novel approach for GSR detection via microscopic-attenuated total reflectance (ATR) Fourier transform infrared (FT-IR) spectroscopic imaging was investigated by applicants. ATR-FT-IR analysis of GSR is nondestructive, with analysis times competitive to current methodologies, and offers a molecular "fingerprint" of the detected GSR. The vibrational signatures collected from the tape substrate and GSR particles (both OGSR and IGSR) are easily discernible by the naked eye. Furthermore, this vibrational "fingerprint" targets a wider range of chemicals compared to current methodologies, increasing the selectivity of the method. The optics of ATR-FT-IR imaging provides pseudo-immersion analysis. The high refractive index (4.0) of the germanium ATR crystal increases the numerical aperture of the optics, enhancing spatial resolution by a factor of 4, without the use of a synchrotron light source ("ATR Accessories An Overview," *PerkinElmer Life and Analytical Sciences* (2004), which is hereby incorporated by reference in its entirety). Analysis is performed in ambient conditions and may detect GSR regardless of debris collection. Exhaustive research applying micro-ATR-FT-IR chemical imaging (mapping) to the fields of bio-medical (Chan et al., *Appl. Spectrosc.* 59:149 (2005); Anastassopoulou et al., *Vibrational Spectroscopy* 51:270 (2009); Kazarian et al., *Biochimica et Biophysica Acta (BBA)—Biomembranes* 1758:858 (2006); Kazarian et al., *Analyst* 138:1940 (2013), which are hereby incorporated by reference in their entirety) and forensic research (Dirwono et al., *Forensic Sci. Int'l* 199:6 (2010); Ng et al., *Anal. and Bioanal. Chem.* 394:2039 (2009); Spring et al., *Anal. and Bioanal. Chem.* 392:37 (2008), which are hereby incorporated by reference in their entirety) have been reported. GSR detection via micro-ATR-FT-IR chemical imaging has not previously been investigated, although it has been suggested (Ng et al., *Anal. and Bioanal. Chem.* 394:2039 (2009); Ricci et al., 6402:64020J (2006), which are hereby incorporated by reference in their entirety).

BRIEF DESCRIPTION OF THE DRAWINGS

FIG. 2a shows the visual image of the mapped tape substrate area. FIGS. 2b-d show IR images of the mapped area, each pixel represents one raw ATR-FT-IR spectrum. The pixels are colored by intensities of transmitted light at 1415 $cm^{-1}$ (chemical marker for IGSR), 1646 $cm^{-1}$ (a chemical marker for OGSR), and 1728 $cm^{-1}$ (chemical marker for the tape substrate), respectively. FIG. 2e shows color scale determining the intensities of detected chemical signal. Blue colored areas indicate strong absorption (low % T) by the analyte, at that specific frequency. Red colored areas indicate little to no absorption (high % T) by the analyte, at that specific frequency.

FIG. 3a shows a visual image of the mapped area. FIG. 3b shows characteristic OGSR and tape spectra, green (marked by ●) and red (marked by ◇) traces, respectively. Dotted lines highlight the chemical markers (1628 and 1728 $cm^{-1}$) used for each analyte. FIGS. 3c-d show IR imaging based upon intensity of the ATR-FT-IR spectra at 1628 $cm^{-1}$ (a chemical marker for OGSR) and 1728 $cm^{-1}$ (chemical marker for the tape substrate), respectively. Each pixel was colored by the intensity of transmitted light for that chemical marker (scale is depicted in FIG. 2e).

FIG. 4a shows trend in mapping spectra collected at the boundary of a cotton fiber and a microscopic OGSR particle. Spectra 1 to 4 transition from collection over the cotton substrate to the OGSR particle, with a step size of 1.56 µm. The highlighted regions depict a disappearance in contribution from the cotton substrate (doublet at 1055 and 1031 $cm^{-1}$) and an increase in contribution from the OGSR particle (peak at 1646 $cm^{-1}$). FIG. 4b shows the collection location of spectra plotted in FIG. 4a on the IR image. The arrow is an illustrative approximation of the spectral collection locations. Outlined areas indicate the cotton fiber and OGSR particle. Pixel color was based upon the intensity of the ATR-FT-IR band at 1728 $cm^{-1}$ (chemical marker for the tape substrate).

FIG. 5a shows ATR-FT-IR spectrum collected from the OGSR. The spectrum is characteristic of a nitrate ester explosive. These explosives are the main fuel source in ammunition propellants. FIG. 5b shows EDS spectrum of the OGSR particle with elemental peak assignments. The elemental spectrum obtained from the GSR particle illustrates that its composition is mainly carbon and oxygen with trace amounts of aluminum and lead.

FIG. 8a shows the model with two GSR classes (OGSR and IGSR). FIG. 8b shows spectra for all morphologies of GSR when they are treated as one class. Each data point is the representation of one Raman spectrum. The x and y-axes plot the first and second principal components' impacts (respectively) on each experimental spectrum. Raman data collected from larger GSR particles (OGSR) are represented by blue crosses, data collected from smaller GSR particles (IGSR) are represented by white diamonds and the spectra from the substrate (tape) are represented by upright black triangles with red borders. The ellipsoids around each group represent 99% confidence intervals

FIG. 10a shows visual image of an OGSR particle with an approximate diameter of 60 µm. The red rectangle defines the mapped area. FIG. 10b shows chemical map generated from the mapped area of FIG. 10a, colored by the intensity of the Raman band at approximately 810 cm$^{-1}$, characteristic of the polypropylene tape substrate. FIG. 10c shows three-dimensional chemical map. The x and y-axes represent the coordinates of the map while the z-axis is the projection of the intensity of the Raman band at approximately 1290 cm$^{-1}$, characteristic of OGSR. FIG. 10d shows color scale corresponding to Raman peak intensity in the chemical maps.

DETAILED DESCRIPTION OF THE INVENTION

Figure 1:
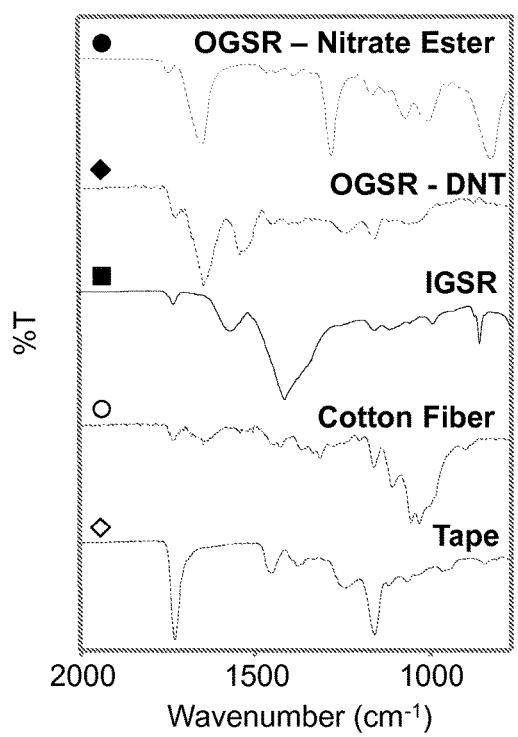
FIG. 1 shows a region of raw ATR-FT-IR spectra collected from GSR particles and the substrates used for GSR collection. Spectra collected from GSR particles are depicted in the green (marked by ●), blue (marked by ♦), and black traces (marked by ■). The purple (marked by ○) and red (marked by ◇) traces represent an ATR-FT-IR spectrum collected from a cotton fiber and the acrylic polymer of the PSA tape, respectively. GSR spectra were extracted from ATR-FT-IR images of particles which were automatically recorded over arbitrary areas of the tape substrate.

One aspect of the present invention relates to a method of detecting inorganic gunshot residue (GSR) particles. The method includes providing a sample comprising gunshot residue, subjecting the sample to spectroscopic analysis to produce a spectroscopic signature for the sample, and identifying inorganic gunshot residue particles based on the spectroscopic signature for the sample.

In the present invention, the term "spectroscopic signature" refers to a single spectrum, an averaged spectrum, multiple spectra, multidimensional signature, or any other spectroscopic representation of the sample.

In the present invention, the term "sample" refers to a cloth substrate, piece of clothing, piece of tape, piece of tape adhered to a glass slide, or any other substrate, which can potentially contain GSR particles.

In one embodiment, the inorganic gunshot residue particle has a size of 0.2 µm to 1000 µm. In another embodiment, the inorganic gunshot residue particle has a size of 0.2 µm to 10 µm. In another embodiment, the inorganic gunshot residue particle has a size of 10 µm to 1000 µm.

The method of the present invention further includes identifying organic gunshot residue particles based on the spectroscopic signature for the sample. The organic gunshot residue particle has a size of 0.2 µm to 1000 µm.

In yet another embodiment, the organic gunshot residue particle has a size of 0.2 µm to 10 µm. Alternatively, the organic gunshot residue particle has a size of 10 µm to 1000 µm.

The spectroscopic analysis can involve Raman spectroscopy, vibrational spectroscopy, and combinations thereof. The Raman spectroscopy can be NIR Raman spectroscopy or Surface Enhanced Raman spectroscopy (SERS).

Raman spectroscopy is a spectroscopic technique which relies on inelastic or Raman scattering of monochromatic light to study vibrational, rotational, and other low-frequency modes in a system (Gardiner, D. J., *Practical Raman Spectroscopy* Berlin: Springer-Verlag pp. 1-3 (1989), which is hereby incorporated by reference in its entirety). Vibrational modes are very important and very specific for certain types of chemical bonds in molecules. They provide a "fingerprint" by which a molecule can be identified. The Raman effect is obtained when a photon interacts with the electron cloud of a molecular bond exciting the electrons into a virtual state. The scattered photon is shifted to lower frequencies (Stokes process) or higher frequencies (anti-Stokes process) as it releases energy to or from the molecule, respectively. The polarizability change in the molecule will determine the Raman scattering intensity, while the Raman shift will be equal to the vibrational energy involved.

Raman spectroscopy is based upon the inelastic scattering of photons or the Raman shift (change in energy) caused by molecules. The analyte is excited by laser light and upon relaxation scatters radiation at a different frequency which is collected and measured. With the availability of portable Raman spectrometers, it is possible to collect Raman spectra in the field. Using portable Raman spectrometers offers distinct advantages to government agencies, first responders, and forensic scientists (Hargreaves et al., *J. Raman Spectroscopy* 39 (7):873-880 (2008), which is hereby incorporated by reference in its entirety). Stich, et al. identified several components of GSR particles via Raman spectrometry with results consistent with SEM/EDX analysis (Stich et al., *J. Raman Spectroscopy* 29 (9):787-790 (1998), which is hereby incorporated by reference in its entirety). Conclusions from their experiment illustrate that Raman spectrometry is able to contribute in a swift and cost effective way to the armory of the modern forensic science laboratory.

Fluorescence interference is the largest problem with Raman spectroscopy and is perhaps the reason why the latter technique has not been more popular in the past. If a sample contains molecules that fluoresce, the broad and much more intense fluorescence peak will mask the sharp Raman peaks of the sample. There are a few remedies to this problem. One solution is to use deep ultraviolet (DUV) light for exciting Raman scattering (Lednev I. K., "Vibrational Spectroscopy: Biological Applications of Ultraviolet Raman Spectroscopy," in: V. N. Uversky, and E. A. Permyakov, *Protein Structures, Methods in Protein Structures and Stability Analysis* (2007), which is hereby incorporated by reference in its entirety). Practically, no condensed face exhibits fluorescence below ~250 nm. Possible photodegradation of biological samples is an expected disadvantage of DUV Raman spectroscopy. Another option to eliminate fluorescence interference is to use a near-IR (NIR) excitation for Raman spectroscopic measurement. Finally, surface enhanced Raman spectroscopy (SERS) which involves a rough metal surface can also alleviate the problem of fluorescence (Thomas et al., "Raman Spectroscopy and the Forensic Analysis of Black/Grey and Blue Cotton Fibers Part 1: Investigation of the Effects of Varying Laser Wavelength," *Forensic Sci. Int'l.* 152:189-197 (2005), which is hereby incorporated by reference in its entirety). However, this method requires direct contact with the analyte and cannot be considered to be nondestructive.

Basic components of a Raman spectrometer are (i) an excitation source; (ii) optics for sample illumination; (iii) a single, double, or triple monochromator; and (iv) a signal processing system consisting of a detector, an amplifier, and an output device.

Typically, a sample is exposed to a monochromatic source usually a laser in the visible, near infrared, or near ultraviolet range. The scattered light is collected using a lens and is focused at the entrance slit of a monochromator. The monochromator, which is set for a desirable spectral resolution rejects the stray light in addition to dispersing incoming radiation. The light leaving the exit slit of the monochromator is collected and focused on a detector (such as a photodiode arrays (PDA), a photomultiplier (PMT), or charge-coupled device (CCD)). This optical signal is converted to an electrical signal within the detector. The incident signal is stored in computer memory for each predetermined frequency interval. A plot of the signal intensity as a function of its frequency difference (usually in units of wavenumbers, $cm^{-1}$) will constitute the Raman spectroscopic signature.

Raman signatures are sharp and narrow peaks observed on a Raman spectrum. These peaks are located on both sides of the excitation laser line (Stoke and anti-Stoke lines). Generally, only the Stokes region is used for comparison (the anti-Stoke region is identical in pattern, but much less intense) with a Raman spectrum of a known sample. A visual comparison of these set of peaks (spectroscopic signatures) between experimental and known samples is needed to verify the reproducibility of the data. Therefore, establishing correlations between experimental and known data is required to assign the peaks in the molecules, and identify a specific component in the sample.

The types of Raman spectroscopy suitable for use in conjunction with the present invention include, but are not limited to, conventional Raman spectroscopy, Raman microspectroscopy, near-field Raman spectroscopy, including but not limited to the tip-enhanced Raman spectroscopy, surface enhanced Raman spectroscopy (SERS), surface enhanced resonance Raman spectroscopy (SERRS), and coherent anti-Stokes Raman spectroscopy (CARS). Also, both Stokes and anti-Stokes Raman spectroscopy could be used.

Scanning Electron Microscopy combined with Energy Dispersive Spectroscopy (SEM/EDS or EDX when equipped with an X-ray analyzer) is capable of obtaining both morphological information and the elemental composition of GSR particles. Recently, SEM/EDS systems have become automated, making automated computer-controlled SEM the method of choice for most laboratories conducting GSR analyses. Several features of the SEM make it useful in many forensic studies, and especially in GSR analysis, including magnification, imaging, composition analysis, and automation (Schwoeble and Exline, "Current Methods in Forensic Gunshot Residue Analysis," CRC Press: New York (2000), which is hereby incorporated by reference in its entirety).

Inductively coupled plasma mass spectrometry (ICP-MS) is a mass analysis method with sensitivity to metals. As a result, this analytical technique is ideal for analyzing barium, lead, and antimony, the major elements commonly found in GSR (Sarkis et al., *Forensic Sci. Int'l* 172 (1):63-66 (2007), which is hereby incorporated by reference in its entirety). This technique is known for its sensitivity, having detection limits that are usually in the parts per billion (Schwoeble et al, "Current Methods in Forensic Gunshot Residue Analysis," CRC Press: New York (2000), which is hereby incorporated by reference in its entirety). ICP-MS has proven to be a fast, precise, and trustworthy analytical method for the confirmation of firearm discharge (Sarkis et al., *Forensic Sci. Int'l* 172 (1):63-66 (2007), which is hereby incorporated by reference in its entirety).

Fourier transform infrared (FTIR) spectroscopy is a versatile tool for the detection, estimation, and structural determination of organic compounds such as drugs, explosives, and organic components of GSR. FTIR can be utilized for the detection of organic gunshot residue (OGSR) at the bullet entrance hole and on the hands and clothing of the shooter. Furthermore, FTIR shows promise in its ability to determine the shooting distance (Sharma et al., *Science & Justice* 49 (3):197-204 (2009), which is hereby incorporated by reference in its entirety). Due to the availability of portable IR spectrometers, it will be possible to analyze OGSR at the crime scene.

Capillary electrophoresis (CE) is another analytical technique that is applied to OGSR analysis. The significant advantage of CE is the low probability of false positives (Bell, S., *Forensic Chemistry*, Pearson Education: Upper Saddle River, N.J. (2006), which is hereby incorporated by reference in its entirety).

Atomic absorption spectroscopy (AAS) is a bulk method of analysis used in the analysis of inorganic materials in primer residue, namely Ba and Sb (Schwoeble and Exline, "Current Methods in Forensic Gunshot Residue Analysis," CRC Press: New York (2000), which is hereby incorporated by reference in its entirety). The high sensitivity for a small volume of sample is one advantage of AAS. This technique involves the absorption of thermal energy by the sample and subsequent emission of some or all of the energy in the form of radiation (Bauer et al., *Instrumental Analysis*, Allyn and Bacon, Inc.: Boston (1978), which is hereby incorporated by reference in its entirety). These emissions are generally unique for specific elements and thus give information about the composition of the sample. The determination of GSR residue by AAS has been used to measure the distribution of GSR particles (Stich et al., *J. Raman Spectroscopy* 29 (9):787-790 (1998), which is hereby incorporated by reference in its entirety). Laser-induced breakdown spectroscopy (LIBS) is a type of atomic emission spectroscopy that implements lasers to excite the sample. Rather than flame AAS, LIBS is accessible to field testing because of the availability of portable LIBS systems.

X-ray diffraction (XRD) is one such technique that can be used for the characterization of a wide variety of substances of forensic interest, including GSR (Abraham et al., *Forensic Sci. Comm.* 9 (2) (2007), which is hereby incorporated by reference in its entirety). XRD is capable of obtaining information about the actual structure of GSR samples, in a non-destructive manor.

In one embodiment, the spectroscopic analysis is vibrational spectroscopy. The vibrational spectroscopy can involve Infrared (IR) absorption, Fourier Transform Infrared absorption (FTIR), or Attenuated Total Reflection (ATR) FTIR.

In another embodiment, the spectroscopic analysis is Attenuated Total Reflectance (ATR) Fourier transform Infrared absorption (FTIR).

In another embodiment, the spectroscopic analysis is microscopic ATR FTIR.

Microscopic-attenuated total reflectance (ATR) Fourier transform infrared (FT-IR) spectroscopic analysis of GSR is nondestructive, with analysis times competitive to current methodologies, and offers a molecular "fingerprint" of the detected GSR. The vibrational signatures collected from the tape substrate and GSR particles (both OGSR and IGSR) are easily discernible by the naked eye. Furthermore, this vibrational "fingerprint" targets a wider range of chemicals as compared to current methodologies, increasing the selectivity of the method. The optics of ATR-FT-IR imaging provides pseudo-immersion analysis. The high refractive index of the germanium ATR crystal increases the numerical aperture of the optics, enhancing spatial resolution by a factor of 4, without the use of a synchrotron light source (ATR accessories An overview, *PerkinElmer Life and Analytical Sciences* (2004), which is hereby incorporated by reference in its entirety). Exhaustive research applying micro-ATR-FT-IR chemical imaging (mapping) to the fields of bio-medical (Chan et al., *Appl. Spectrosc.* 59:149 (2005); Anastassopoulou et al., *Vibrational Spectroscopy* 51:270 (2009); Kazarian et al., *Biochimica et Biophysica Acta (BBA)—Biomembranes* 1758:858 (2006); Kazarian et al., *Analyst* 138:1940 (2013), which are hereby incorporated by reference in their entirety) and forensic research (Dirwono et al., *Forensic Sci. Int'l* 199:6 (2010); Ng et al., *Anal. and Bioanal. Chem.* 394:2039 (2009); Spring et al., *Anal. and Bioanal. Chem.* 392:37 (2008), which are hereby incorporated by reference in their entirety) have been reported. GSR detection via micro-ATR-FT-IR chemical imaging has not previously been investigated, although it has been suggested (Ng et al., *Anal. and Bioanal. Chem.* 394:2039 (2009); Ricci et al., 6402:64020J (2006), which are hereby incorporated by reference in their entirety).

In yet another embodiment, the spectroscopic signature is a multidimensional vibrational signature.

In a further embodiment, the method of the present invention additionally includes determining, from the spectroscopic signature, the type of ammunition and/or the type of weapon used to fire the ammunition from which the gunshot residue is derived.

The type of ammunition determined can be 9 mm caliber, .45 caliber, .40 caliber, .22 L caliber, or .38 Special.

In another embodiment, the method of the present invention further includes comparing the spectroscopic signature for the sample to reference spectroscopic signatures for different types of ammunition and/or types of weapons used to fire the ammunition and characterizing the type of ammunition and/or the type of weapon used to fire the ammunition from the spectroscopic signature of the sample based on said comparing.

A second aspect of the present invention relates to a method of detecting gunshot residue particles. The method includes providing a sample comprising gunshot residue, subjecting the sample to spectroscopic analysis to produce a spectroscopic signature for the sample, where the spectroscopic signature spans a range of wavenumbers, creating one or more spectroscopic maps from the spectroscopic signature for the sample, where each different spectroscopic map is for a different wavenumber, and identifying gunshot residue particles based on the one or more spectroscopic maps for the sample.

In the present invention, the term "spectroscopic map" refers to a map containing information about each spectrum from the spectroscopic signature of the sample, or to a map containing information about peak intensity at a specific wavenumber for each spectrum, or any other spectroscopic representation of the sample.

In one embodiment, the one or more spectroscopic maps are multidimensional vibrational maps.

The spectroscopic maps can be created for specific wavenumbers with the specific wavenumbers being markers for inorganic gunshot residue particles, organic gunshot residue particles, and/or tape substrate. The wavenumbers serving as a marker for inorganic gunshot residue particle include 1415 $cm^{-1}$. The wavenumbers serving as a marker for organic gunshot residue particle include 1646 $cm^{-1}$. The wavenumbers serving as a marker for tape substrate include 1728 $cm^{-1}$.

In a further embodiment, the gunshot residue particle has a size of 0.2 µm to 1000 µm. Alternatively, the gunshot residue particle has a size of 0.2 µm to 10 µm. As yet another alternative, the gunshot residue particle has a size of 10 µm to 1000 µm.

In another embodiment, the method of the present invention further includes determining, from the one or more spectroscopic maps, the type of ammunition and/or the type of weapon used to fire the ammunition from which the gunshot residue is derived. The determining step includes comparing the one or more spectroscopic maps for the sample to reference spectroscopic maps for different types of ammunition and/or types of weapons used to fire the ammunition and characterizing the type of ammunition and/or the type of weapon used to fire the ammunition from the one or more spectroscopic maps for the sample based on said comparing.

Tape lifting was performed over a cloth substrate populated with GSR. Micro-ATR-FT-IR was used to rapidly map an arbitrary 500 µm² area of the tape substrate to determine if GSR was present. For real world forensic purposes, the scanned area may be increased through; an increase in analysis time, or a decrease in spatial resolution or spectral resolution. IR images of the mapped area were generated and colored according to the intensities of specific vibrational modes, or chemical markers, for the rapid detection of each analyte (OGSR, IGSR, and the tape substrate). The results indicate that both OGSR and IGSR particles can be detected on the tape substrate with an approximate spatial resolution of 4.7 µm. The latter value indicates the size-detection limit for GSR particles, which is within a "practically important range" and could be further adjusted if necessary through modifications of the of microscope objective.

These aspects of the present invention are further illustrated by the examples below.

EXAMPLES

The following examples are provided to illustrate embodiments of the present invention but are by no means intended to limit its scope.

Example 1

GSR Collection

GSR samples were generated by discharging 0.38 in. caliber Winchester brand "0.38 special" ammunition from a Smith and Wesson Model 10 Revolver and 0.40 in. Federal brand "S&W" full metal jacketed ammunition from a Smith and Wesson M&P 40 firearm. The firearms were discharged approximately 0.3 m away from a cloth collection substrate. For real world applications of this method, the cloth substrate mimics the clothing of a shooting victim or suspect. 3M brand double-sided PSA tape (common office tape) was utilized for tape lifting. Pieces of tape were adhered to a 1×1 in. glass microscope slide. PSA tape is composed of an acrylic polymer adhesive layer, supported on a hydrocarbon backbone (Toyama et al., *J. of Applied Polymer Sci.* 17:3495 (1973), which is hereby incorporated by reference in its entirety). The available side of the adhesive tape was pressed against the cloth discharge substrate to collect the GSR particles. Several macroscopic (>500 μm diameter) GSR particles were visible to the naked eye on the tape collection substrate. To detect smaller GSR particles collected by the substrate, microscopic-ATR-FT-IR imaging was performed.

Example 2

ATR-FT-IR Microscope

Micro-ATR-FT-IR imaging was performed with a Perkin Elmer Spotlight 400 IR Microscope and Spectrum 10 software. The 1×1 in. glass microscope slides with the adhered tape and GSR samples were placed under the micro-ATR objective. The micro-ATR objective utilized to collect the IR images was composed of a germanium crystal with a 600 μm tip. The tip of the Ge crystal was kept in constant contact with the surface of the samples due to a spring mechanism. This mechanism allowed the crystal to navigate the three-dimensional sample surface. The depth of penetration of the evanescent wave was 0.65 μm. 500 μm$^2$ areas of the tape substrate were mapped individually. A mercury cadmium telluride (MCT) detector array allowed for the collection of an ATR-FT-IR spectrum every 1.56 μm (pixel size). 320 spectra were collected in both the X and Y directions, and, therefore, each IR image is the representation of 102,400 pixels, each corresponding to one ATR-FT-IR spectrum. The Spotlight 400 collected 170 high quality spectra per second. Each spectrum was the average of 4 scans collected over the spectral range of 4000-750 cm$^{-1}$, with a spectral resolution of 4 cm$^{-1}$. Spectra were collected in ATR mode, percent transmittance (% T). The total analysis time for the collection of one IR image was approximately 40 minutes. The spectrum of air (background) was collected before all sample measurements and subsequently removed from the data. Additional atmospheric absorptions were removed with an atmospheric vapor compensation (AVC) function. Noise reduction (principal component analysis (PCA)) was also implemented. The IR images were generated using MATLAB 7.9.0 (MathWorks Inc.).

Example 3

Scanning Electron Microscope

For SEM analysis, OGSR particles with diameters of approximately 500 μm were manually deposited on adhesive carbon discs obtained from Ted Pella, Inc. The discs were mounted on SEM stubs. Police typically use these adhesive discs for GSR collection and detection, since they are conductive, stable under an electron beam and in a vacuum. All of these properties are required for SEM analysis. SEM/EDS analysis was performed by Evans Analytical Group, Inc. A Hitachi 3400-N Variable Pressure SEM with INCA software (Oxford Instruments, Inc.) was used for the acquisition of electron images and collection of elemental spectra (EDS) from several OGSR particles. A magnification of 100× was used to obtain the SEM images. An accelerating voltage of 20 kV was utilized. EDS spectra were collected over a range of 0 to 10 keV.

Example 4

Micro-ATR-FT-IR Spectra of GSR Particles and Substrates

A variety of chemicals are required to successfully expel a projectile from a firearm. These include initiators, oxidizers, and fuels; whose presence is relatively uniform across different brands of ammunition (Dalby et al., *J. of Forensic Sci.*, 55:924 (2010); Schwoeble et al., *Current Methods in Forensic Gunshot Residue Analysis* CRC Press: New York, (2000), which are hereby incorporated by reference in their entirety). Chemicals used more sparingly, which perform unique tasks in ammunition (stabilizers, plasticizer and others), are considered additives. FIG. 1 illustrates the detection of these chemical species in characteristic micro-ATR-FT-IR spectra of OGSR (green and blue traces) and IGSR (black trace) particles. The spectra illustrated in FIG. 1 were extracted from micro-ATR-FT-IR images, which mapped arbitrary areas of the tape substrate for GSR detection (see Micro-ATR-FT-IR Imaging). In total, four GSR particles were detected in two different IR images. The detected particles included one macroscopic OGSR, one microscopic OGSR, and two microscopic IGSR particles. The IGSR particles provided similar spectroscopic signatures (FIG. 1, black trace).

Spectra collected from the macroscopic OGSR particle were found to have high contributions of nitrate ester explosives (R—O—NO$_2$ containing groups), FIG. 1, green trace. Intense IR bands at approximately 1628, 1270, and 816 cm$^{-1}$ are characteristic to NO$_2$ symmetric stretching, asymmetric stretching, and NO stretching, respectively, of the nitrate group inherent to these partially burnt explosives (Banas et al., *Anal. Chem.* 82:3038 (2010); Kovalenko et al., *J. of Structural Chem.* 34:540 (1994), which are hereby incorporated by reference in their entirety). Nitrate esters are common to OGSR, as they represent the base and main fuel source for modern smokeless ammunition propellants. The blue trace represents an ATR-FT-IR spectrum collected from a microscopic OGSR particle with an approximate diameter of 25 μm. Both the 1646 and 1532 cm$^{-1}$ bands were assigned to the asymmetric stretching in-plane ring vibration coupled with NO$_2$ asymmetric stretching for 2,4-dinitrotoluene (2,4-DNT) (Ramos et al., *J. of Molecular Structure: THEOCHEM* 769:69 (2006); López-López et al., *Anal. Chimica Acta* 717:92 (2012), which are hereby incorporated by reference in their entirety). 2,4-DNT is used as a flash suppressant, a specific additive in ammunition propellants (Dalby et al., *J. of Forensic Sci.* 55:924 (2010); Wallace, *Chemical Analysis of Firearms, Ammunition, and Gunshot Residue;* CRC Press: Boca Raton, (2008), which are hereby incorporated by reference in their entirety), and contributes to OGSR. The black trace in FIG. 1 is representative of a GSR particle with a diameter of approximately 30 μm. Prominent bands occur at approximately 1567, 1415, 993, and 856 cm$^{-1}$. These bands were preliminarily assigned to the fundamental vibrations; $v_2+v_{4a}$, $332+v_1$, $v_1$ and $v_2$, respectively, of the coordinated carbonate ion (CO$_3^{2-}$) originating from metal-carbonate complexes (Andersen et al., *Acta Chem. Scand.* 45:1018 (1991), which is hereby incorporated by reference in its entirety). Carbonate complexes originate from both the primer and propellant of the ammunition, acting as stabilizers and neutralizers and contributing to IGSR. The percent composition of carbonate mixtures in different ammunition was found to range from nonexistent to 0.4% (Wallace, *Chemical Analysis of Firearms, Ammunition, and Gunshot Residue;* CRC Press: Boca Raton, (2008), which are hereby incorporated by reference in its entirety). It is well established that the chemical composition of the original ammunition directly impacts the chemical nature of the resulting GSR particles. Therefore, more uncommon chemicals (propellant additives) may be used as chemical markers to identify GSR particles originating from specific ammunition, or to discriminate GSR particles originating from different ammunition (López-López et al., *Anal. Chem.* 84:3581 (2012), which is hereby incorporated by reference in its entirety).

Several cotton fibers from the original discharge collection surface were recovered as "debris" during tape lifting. The purple trace in FIG. 1 is a micro-ATR-FT-IR spectrum collected from a cotton fiber. The doublet at 1055 and 1031 cm$^{-1}$ was assigned to the asymmetric stretching of the cellulose ring and C—O stretching, respectively (Chung et al., *Carbohydrate Polymers* 58:417 (2004), which is hereby incorporated by reference in its entirety). The depth of analysis for micro-ATR-FT-IR was approximately 0.65 µm. Thus only the acrylic polymer from the top layer of the tape was probed in the resulting ATR-FT-IR data (FIG. 1, red trace). The peak locations of the carbonyl stretching (1728 cm$^{-1}$) and asymmetric stretching vibrations of the C—O—C group (1190 cm$^{-1}$), are characteristic to the acrylic polymer; poly(methyl acrylate) or PMA (Willis et al., *Polymer* 10:737 (1969), which is hereby incorporated by reference in its entirety). It is clearly illustrated that the ATR-FT-IR spectra of the GSR particles contain unique vibrational modes, which are not present in the ATR-FT-IR spectra of the substrate or debris. IR imaging was implemented to isolate these unique bands for automated detection of GSR on the tape substrate.

Example 5

Micro-ATR-FT-IR Imaging

An arbitrary (random) 500 µm$^2$ area of the tape substrate was visually imaged after tape lifting (FIG. 2a). Although the cotton fibers collected from the original substrate are apparent in the visual image, the presence or absence of GSR particles is difficult to determine as they may be camouflaged by the substrate. IR imaging was performed over the same area. One ATR-FT-IR spectrum was collected every 1.56 µm. The IR images are represented in FIGS. 2b-d. Each pixel represents one raw micro-ATR-FT-IR spectrum. The color of the pixel is determined by the peak intensity at a specific frequency of mid-IR radiation. As illustrated by the color scale (FIG. 2e), blue colored areas indicate strong absorption (low % T and high chemical signal) by the analyte, at that specific frequency. Red colored areas indicate little to no absorption (high % T) by the analyte, at that specific frequency.

Figure 2:
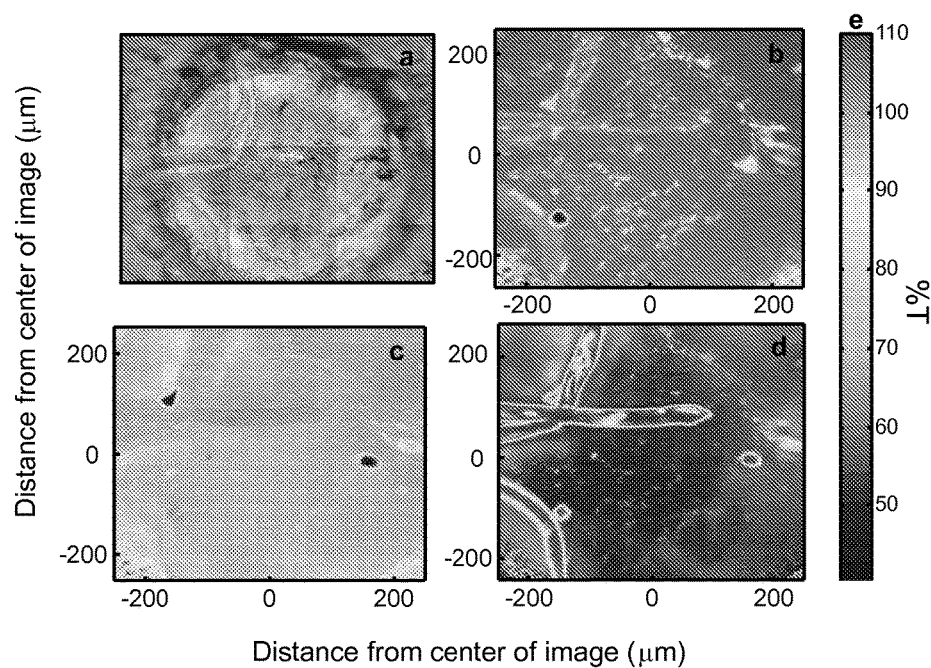
FIGS. 2 a-e show IR imaging for detection of microscopic GSR.

Three frequencies of absorbed radiation were selected as chemical markers for the detection of microscopic IGSR, OGSR, and the tape substrate within the mapped area. FIG. 2b illustrates the detection of an IGSR particle with an approximate diameter of 30 µm. The IR band at approximately 1415 cm$^{-1}$ (FIG. 1, black trace) was used as a chemical marker for IGSR detection. This band was preliminary assigned to a fundamental vibrational mode of a carbonate ion, which is characteristic to IGSR (Andersen et al., *Acta Chem. Scand.*, 45:1018 (1991), which is hereby incorporated by reference in its entirety). IGSR strongly absorbs (low % T) light at this frequency while the tape substrate does not (FIG. 1, red trace). The ATR-FT-IR spectra collected over the IGSR particle are shaded with blue hues, making the IGSR particle clearly visible against the red background of the tape substrate. Similar results are illustrated for the detection of OGSR (FIG. 2). OGSR particles which were not observed in the visual image are clearly illustrated in the IR map (FIG. 2c, two blue colored circles). ATR-FT-IR pixels in FIG. 2c are colored by the intensity of the band at approximately 1646 cm$^{-1}$ (ring stretching, originating from 2,4-DNT) (Ramos et al., *J. of Molecular Structure: THEOCHEM*, 769:69 (2006), which is hereby incorporated by reference in its entirety). The carbonyl stretching band characteristic to the tape substrate (PMA) at 1728 cm$^{-1}$ (Willis et al., *Polymer* 10:737 (1969), which is hereby incorporated by reference in its entirety) was used to color the IR image in FIG. 2d. The red colored areas indicate that the cotton fibers, OGSR, and IGSR particles do not strongly absorb (high % T) in this region of the spectrum. It is interesting to note that the cotton fibers do not inhibit the detection of OGSR or IGSR particles. FIGS. 2b-c illustrate that the fibers are nearly invisible as compared to the blue colored GSR particles. Therefore, micro-ATR-FT-IR imaging is not susceptible to debris interferences, in contrast to the current GSR detection methodology.

Figure 3:
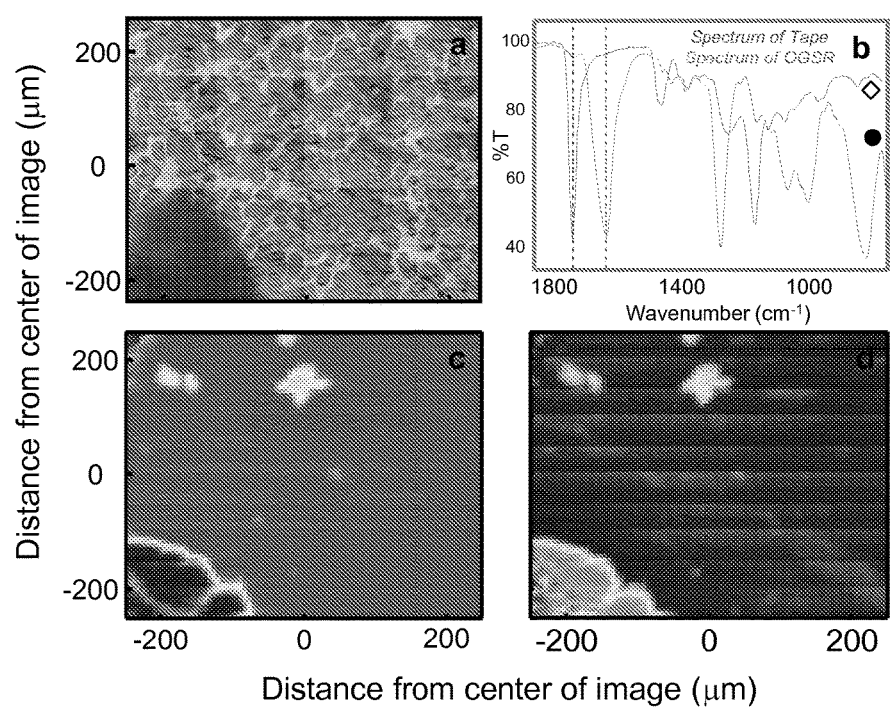
FIGS. 3a-d show IR imaging for macroscopic OGSR detection.

IR imaging was applied to areas of the tape substrate populated by macroscopic OGSR (FIG. 3). Although larger GSR particles may be visible to the naked eye, for real world applications of this method, micro-ATR-FT-IR imaging provides chemical detection of GSR, without any bias from the forensic investigator. Tape lifting was performed over areas of the cloth substrate visually populated by GSR. The visual image (FIG. 3a) of the mapped area illustrates a macroscopic OGSR particle. FIG. 3b plots the characteristic ATR-FT-IR spectra collected from the OGSR particle and tape substrate (green and red traces, respectively). The green dotted line highlights the IR peak used to color the IR image in FIG. 2c. The peak at 1628 cm$^{-1}$ was assigned to the NO$_2$ asymmetric stretching and is a chemical marker for OGSR (Kovalenko et al., *J. of Structural Chem.* 34:540 (1994); López-López et al., *Anal. Chimica Acta* 717:92 (2012), which are hereby incorporated by reference in their entirety). The blue colored pixels in FIG. 3c illustrate the detection of a macroscopic OGSR particle. The red dotted line in FIG. 3b highlights the chemical marker used for the detection of the tape substrate. The IR image in FIG. 3d is colored by the intensity of transmitted light for the carbonyl stretching mode (1728 cm$^{-1}$) characteristic to the tape substrate (PMA).

Macroscopic OGSR particles originating from the two different discharger samples investigated in this study (see GSR Collection), were previously found to give similar (to the naked eye) ATR-FT-IR spectra, which required advanced statistics to discriminate (Bueno et al., *Anal. Chem.* 85:7287 (2013), which is hereby incorporated by reference in its entirety). However, differences in the spectroscopic signatures of macro and microscopic OGSR particles are not surprising. Smokeless ammunition propellant particles are composed of a base of nitrate ester explosives, with minor contribution of other chemical additives. This base is represented by propellant particles ranging in size from 0.2 to 3 mm, which are not completely consumed (burned) during the firearm discharge process (Pun et al., *Forensic Sci. Int'l* 175:179 (2008), which is hereby incorporated by reference in its entirety). Macroscopic OGSR consist of these incompletely burnt propellant particles. Chemical additives (such as 2,4-DNT) are used in much lower concentrations and may dissociate from the propellant particles during the firearm discharge or originate from the primer of the ammunition.

The morphology of the detected GSR particles is relevant due to the differences between organic and inorganic GSR. IGSR is commonly composed of Pb, Ba and Sb particles resulting in the condensation of these elements after the high temperatures of the discharge process into spheroidal particles. These particles were characterized in this study, as illustrated by the blue circle in FIG. 2b. Conversely, OGSR consists of burnt and partially burnt propellant particles. The shapes of the particles are dependent upon the shape of the original propellant grains. Spheroidal propellant grains are common; however, their diameters are typically much larger than molten IGSR particles (500 μm diameters as compared to 3-20 μm). These morphologies of OGSR were also detected as illustrated by the particle with a triangle shape in FIG. 2c. Here, a novel approach is reported for the collection of both chemical and morphological information from the sample.

Figure 4:
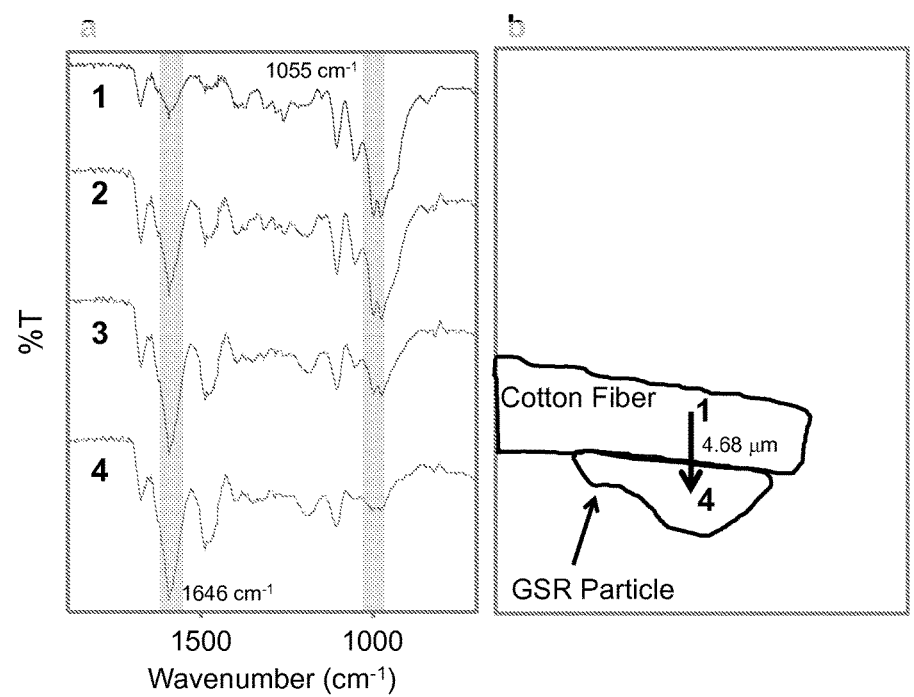
FIGS. 4a-b show spatial resolution of the micro-ATR-FT-IR approach.

The spatial resolution or the ability of the microscope to discern two adjacent chemicals within a specified distance was used to determine the limit of detection for the technique. The spatial resolution was calculated by comparing spectra collected at the boundary of a cotton fiber and a microscopic OGSR particle. FIG. 4a plots spectra transitioning from collection location over the fiber to an OGSR particle. FIG. 4b illustrates a zoomed in image of the IR image, plotting the approximate collection path (vertical arrow) of the spectra in FIG. 4a. Over a distance of approximately 4.7 μm, the spectral contribution from the cotton fiber (doublet at 1055 and 1031 $cm^{-1}$) disappears, and the contribution from the OGSR particle increases (band at 1646 $cm^{-1}$). The bands originating from the cotton fiber, at 1055 and 1031 $cm^{-1}$, were assigned to the asymmetric stretching of the cellulose ring and C—O stretching, respectively (Chung et al., *Carbohydrate Polymers* 58:417 (2004), which is hereby incorporated by reference in its entirety). The technique has an estimated spatial resolution of approximately 4.7 μm. Explicitly, any GSR particle sized of 4.7 μm or greater will be resolved from the collection substrate (tape or cotton) in the IR image.

All spectra in FIG. 4a contain the peaks at approximately 1728 and 1158 $cm^{-1}$. These peaks remain throughout the entire spectroscopic map, independent of the analyte in contact with the ATR crystal. The peaks originate from the carbonyl stretch and C—O—C asymmetric stretching, respectively, from the PMA polymer of the tape substrate (Willis et al., *Polymer* 10:737 (1969), which is hereby incorporated by reference in its entirety). The two most intense peaks originating from PMA (FIG. 1, red trace) are also present in the ATR-FT-IR spectra from each other analyte (FIG. 1, green, blue, black, and purple traces). Conceivably, portions of the tape polymer were adhered to the ATR crystal throughout the entire experiment and thus provided the signal. However, the substrate signal did not block informative vibrational bands from the individual GSR particles. Therefore, no inferences were observed when generating the IR images that targeted informative IR bands.

SEM/EDS is the most common technique for IGSR detection due to its high affinity for detecting Pb, Ba and Sb. However, elemental spectroscopy has little to offer for OGSR analysis. To illustrate the novelty of the micro-ATR imaging approach reported here, the same OGSR particles were analyzed with both vibrational (ATR-FT-IR) and elemental (EDS) spectroscopies.

Figure 5:
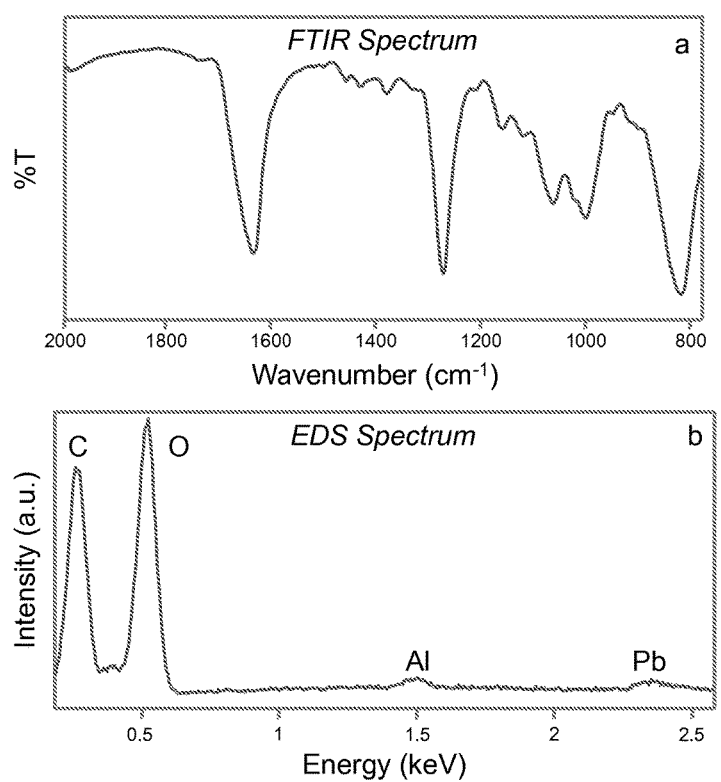
FIGS. 5a-b show vibrational and elemental spectra collected from the same OGSR particle.
Figure 6:
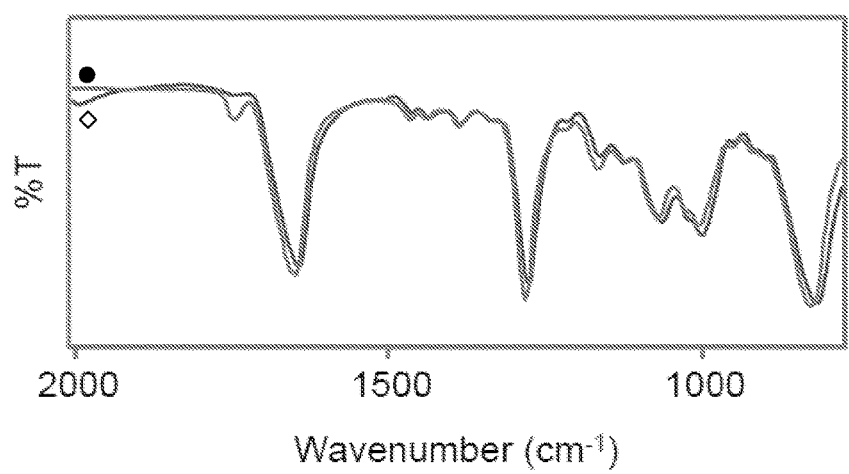
FIG. 6 shows comparison of ATR-FT-IR spectra of the OGSR particles analyzed in FIG. 3 (green trace, (marked by ●)) and the OGSR particle analyzed in FIG. 5 (red trace, (marked by ◇)). The particles originated from the same discharge sample and have the same spectroscopic signature. The red FT-IR spectrum was collected with a PerkinElmer Spectrum 100 FTIR spectrometer. The green spectrum was collected with a PerkinElmer Spotlight 400 IR Microscope.
Figure 7:
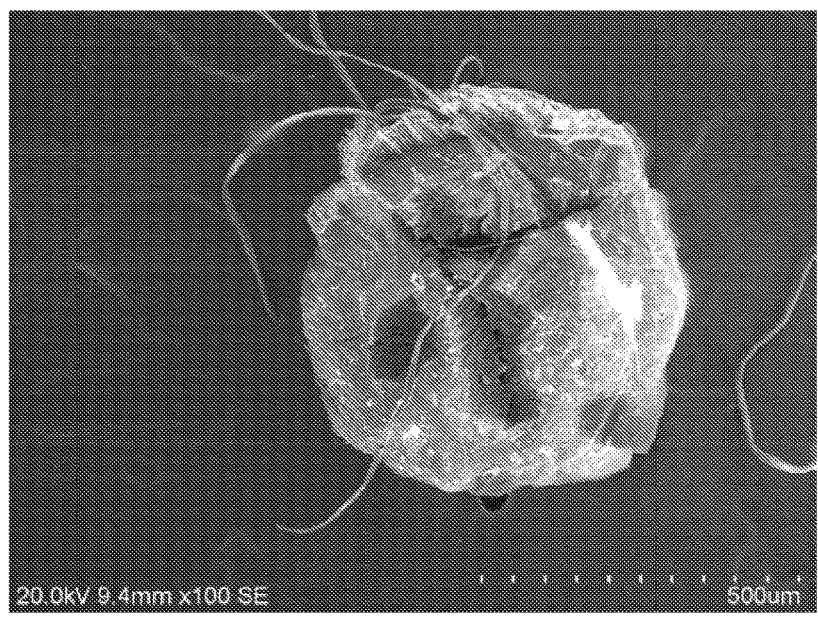
FIG. 7 shows SEM image of the GSR particle subjected to FT-IR and EDS spectroscopy as illustrated in FIG. 5.

An OGSR particle with a diameter of 500 μm was collected from the same discharge sample as the particle analyzed in FIG. 3. This particle was subjected to ATR-FT-IR analysis (FIG. 5a). Results indicate that this particle had the same spectroscopic signature as the particle analyzed in FIG. 3 (FIG. 6). Next, the particle was manually deposited on an adhesive carbon disc for SEM analysis. High resolution SEM images were obtained from the particle (FIG. 7). The elemental composition of the OGSR particle was determined by EDS analysis (FIG. 5b). As indicated by the intense peaks at approximately 0.26 and 0.52 keV, the elemental composition of the OGSR particle was determined to mainly be composed of carbon and oxygen, respectively. Trace amounts of aluminum and lead are represented by the smaller peaks located at approximately 1.5 and 2.3 keV, respectively. When comparing the vibrational and elemental spectra collected from the same OGSR particle, the differences in specificity for each approach become apparent. As described in Micro-ATR-FT-IR Imaging section, the vibrational spectrum is characteristic of nitrate ester explosives, which are common to OGSR or clandestine explosives. Both of these samples have forensic relevance and low probability to exist in the environment as false positives. However, the elemental spectrum indicates that the particle is composed of carbon and oxygen, two elements which are ubiquitous in the environment. Thus, EDS analysis of OGSR offers low specificity. Moreover, the trace detection of aluminum and lead is not sufficient to assign the particle as GSR by current guidelines. These guidelines require a minimum of the detection of two of the three aforementioned heavy metals (Pb, Ba and/or Sb) for a particle to be assigned as GSR (ASTM E 1588-95. In *Annual Book of ASTM Standards;* American Society for Testing and Materials: West Conshohocken, Pa. (2010) and *Guide for Primer Gunshot Residue Analysis by Scanning Electron Microscopy/Energy Dispersive X-Ray Spectrometry;* Scientific Working Group for Gunshot Residue: San Antonio, Tex. (2011), which are hereby incorporated by reference in their entirety). This procedure was repeated with three additional OGSR particles, yielding near identical spectra.

Microscopic-ATR-FT-IR spectroscopic imaging was applied for the automated detection of macro and microscopic OGSR and IGSR particles collected via "tape lifting." Each IR image was the composition of 104,200 micro-ATR-FT-IR spectra. Individual spectra were extracted from the maps to determine the "vibrational fingerprints" of each analyte and to determine the spatial resolution of the technique. Results were reported in IR imaging (chemical maps), colored by the intensity of specific chemical markers for each analyte.

The novel approach provides several improvements over current elemental analyses used for GSR detection. Collection materials (tape) are considerably less expensive, the recovery of debris (cotton fibers) during tape lifting did not inhibit the visualization of the GSR particles and a much wider range of chemicals were targeted reducing the risk of false positive/negative assignments. Specific chemical additives (2,4-dinitrotoluene and metal carbonate complexes) were detected in microscopic GSR. These propellant and primer additives are not uniform across all ammunition. Therefore, the ability to detect these chemicals may indicate that a specific ammunition brand was discharged (or was not) during a shooting incident. Additionally, detection of explosive particles (2,4-DNT) may have applications in the fields of home land security and counter-terrorism.

The area scanned for current GSR detection methods (ASTM standard) (ASTM; American Society for Testing and Materials (2010), which is hereby incorporated by reference in its entirety) is dependent upon the number "characteristic" particles (composed of Pb, Ba, and Sb) which have been detected. This is required because the presence of one particle composed of these heavy metals may originate from an environmental contaminant or specific manufacturing trade. However, detection of multiple particles is more indicative to the presence of true GSR. The detection of one particle composed of a nitrate ester, propellant or primer additive offers higher selectivity for the presence of GSR, as these compounds are not often found in the environment. For this study, each IR image was the composition of 102,400 ATR-FT-IR spectra collected over an area of 500 µm². The amount of time require to locate a GSR particle on the tape substrate is directly related to the number of spectra collected. Therefore, the time required to detect a GSR particle may be reduced if larger pixel sizes (fewer collected ATR-FT-IR spectra) are used to generate the spectroscopic maps. The use of larger pixel sizes has the potential to weaken the spatial resolution of the method.

The spatial resolution of the micro-ATR-FT-IR imaging was determined to be 4.7 µm. Thus, any GSR particle sized 4.7 µm or larger will be resolved from the tape substrate and observable in the IR image when targeting their specific chemical marker.

Example 6

Raman Microscope

A Thermo Fisher Scientific DXR Raman microscope equipped with an Olympus brand microscope and a 50× long working distance objective was used for Raman measurements. A 780 nm Raman excitation laser with a power of 7.5 mW (on the sample) was used for sample analysis. All Raman spectra were collected over a spectral range of 3300-100 $cm^{-1}$ and truncated to a fingerprint range of approximately 1850-320 $cm^{-1}$ for statistical analyses. Raman spectra were the average of five accumulations of twenty seconds each. The enclosed microscope limited potential interferences from cosmic radiation. The diameter of the excitation laser beam was estimated at 1.7 µm. A 3 µm step size was utilized for Raman mapping. Autofocusing based on Raman spectral intensity corrected the z-direction of the microscope at each mapping point. OMNIC 8 software (Thermo Fisher Scientific Inc.) was used to preprocess the experimental spectra and generate the chemical maps. Further preprocessing and statistical analyses of Raman spectra were performed using MATLAB 7.9.0 (MathWorks Inc.) with the PLS toolbox (Eigenvector Research Inc.) Preprocessing of the Raman spectra included Savitsky-Golay smoothing, $6^{th}$ order polynomial baseline correction, normalization by area and mean centering. After preprocessing, spectra with high Q residual and Hotelling $T^2$ values (define the limits of the dataset), were identified as outliers and removed from the training set (Wise et al., PLS Toolbox 3.5 for Use with MATLAB™. Eigenvector Research, Inc., Manson (2004), which is hereby incorporated by reference in its entirety).

Example 7

GSR Samples for Raman Microscope Analysis

Conventional ammunition (heavy metal containing) was utilized. Three 0.38 inch (in.) caliber discharge samples were produced by discharging Winchester brand "0.38 special" ammunition from a Smith and Wesson Model 10 Revolver. A cotton collection substrate at a distance of 0.3 m was used for GSR collection. For real world applications of this method, the cloth substrate mimics the clothing of a shooting victim or suspect. Double-sided pressure-sensitive adhesive tape was utilized for tape lifting. Glass microscope slides were covered with aluminum foil and the tape was adhered to the slide. The available side of the adhesive tape was pressed against the cloth discharge substrate to lift the GSR particles. Several macroscopic (>500 µm diameter) GSR particles were visible to the naked eye on the tape collection substrate. To detect smaller GSR particles collected by the substrate, montage imaging was performed.

Example 8

Raman Spectroscopic Training Set

Three tape swatches were analyzed via Raman mapping, totaling 186 spectra. This constituted the Raman training set data of tape. For the OGSR training set, three OGSR particles were mapped totaling 189 Raman spectra. All OGSR particles analyzed for the training set originated from the same discharge sample. Montage imaging was used to locate smaller (IGSR) particles. A 2 mm² area of the "clean" tape substrate was imaged via montage mapping before lifting. After the lifting, the 2 mm² area montage was collected again. Due to the stage calibration, these two montage images were collected from exactly the same tape area. The two images were compared to determine if any GSR particles were collected. Particles located in the montage image of the tape substrate post lifting, which were not evident in the original image, were subjected to Raman spectroscopic analysis. Particles which exhibited Raman spectra characteristic of primer particles were added to the IGSR training set. It was determined that when the laser spot diameter fell within the boundaries of the particle, no spectral contribution from the substrate was collected. 410 Raman spectra were collected from five different IGSR particles. Therefore, the Raman training set totaled 785 spectra.

Figure 8:
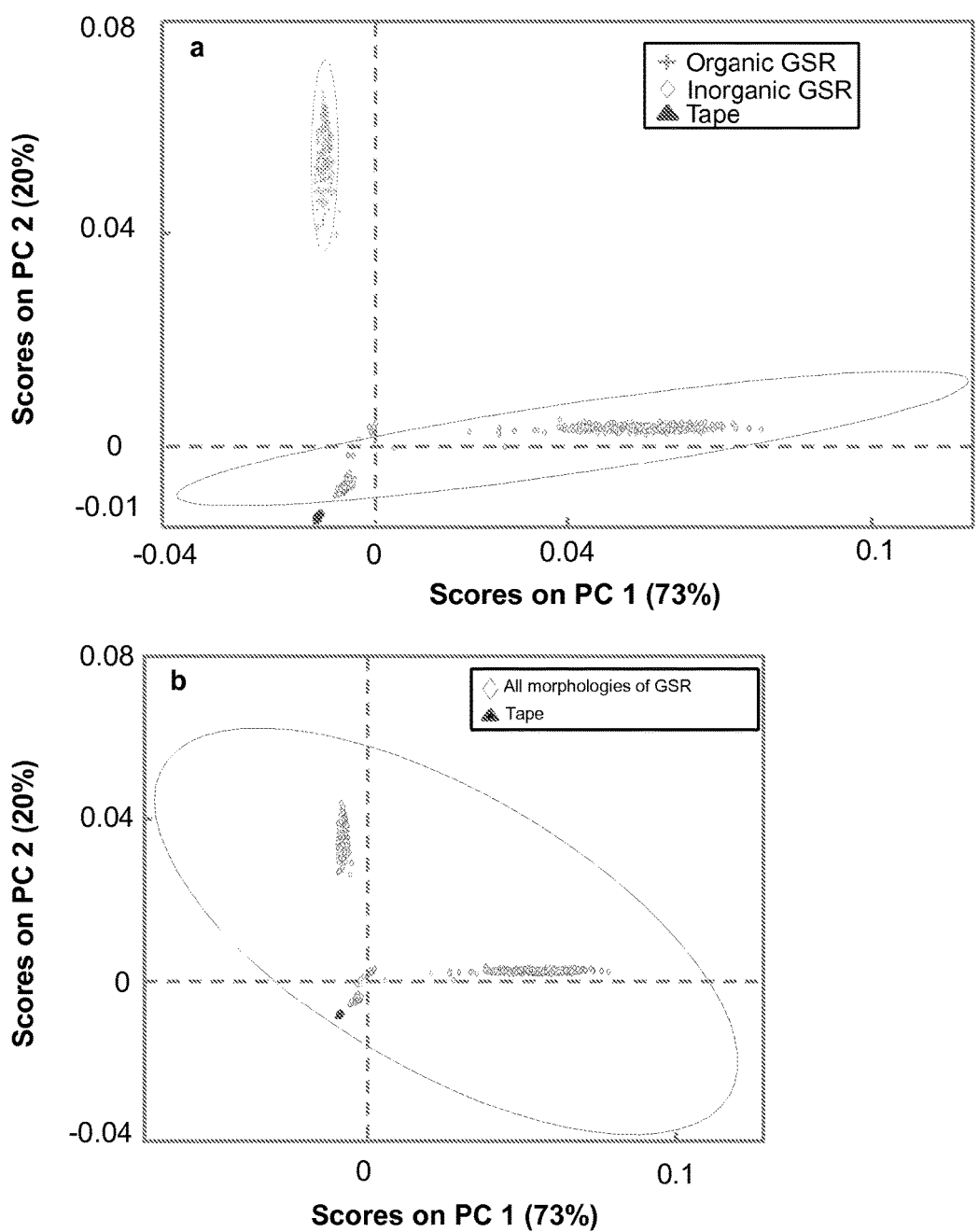
FIGS. 8a-b show principal component analysis (PCA) scores plot treating the three Raman spectroscopic training sets.

There is a known distinction between OGSR and IGSR (Dalby et al., *J. of Forensic Sci.*, 55:924-943 (2010), which is hereby incorporated by reference in its entirety). IGSR consists mainly of heavy metals, inorganic salts and graphite. OGSR particles consist of explosives, plasticizers, stabilizers, and other chemicals common to ammunition propellants. Organic or propellant particles are often larger than IGSR, ranging in size from visible particles to fine dust (Meng et al., *J. of Forensic Sci.*, 42:553-570 (1997), which is hereby incorporated by reference in its entirety). Both types of GSR may be generated from the same firearm discharge. Therefore, the GSR training set was broken into two individual groups: spectra originating from OGSR and IGSR particles. Further justification for generating two spectroscopic training sets is illustrated in FIG. 8. FIG. 8 illustrates justification for considering OGSR and IGSR as different classes. FIG. 8a is a principal component analysis (PCA) scores plot, treating spectra collected from OGSR and IGSR as individual classes with their own confidence intervals. This model is capable of discriminating the three classes with 99% confidence, as none of the ellipsoids overlap. FIG. 8b represents spectra for all morphologies of GSR when they are treated as one class. The model in FIG. 8b is incapable of differentiating Raman spectra collected from GSR particles and the tape substrate with 99% confidence. The OGSR particles were found to have large contribution of nitrate ester explosives (Lewis et al., *Appl. Spectrosc.* 51:1854-1867 (1997), which is hereby incorporated by reference in its entirety). Determining the contributions of nitrate ester explosives in OGSR with Raman spectroscopy is well established (Bueno et al., *Anal. Chem.*, 84:4334-4339 (2012), which is hereby incorporated by reference in its entirety). The Raman spectra collected from the OGSR particles analyzed in this study show two strong bands at 1288 and 1658 $cm^{-1}$, which are characteristic of the symmetric and asymmetric stretching (respectively) of the $NO_2$ groups of nitrate ester explosives. The specific peak locations for these bands are characteristic of the nitrate ester pentaerythritol tetranitrate (PETN) (Lewis et al., *Appl. Spectrosc.* 51:1854-1867 (1997), which is hereby incorporated by reference in its entirety). IGSR provided an intense Raman band at approximately 1575 cm$^{-1}$, assigned to the $E_{2g}$ mode of graphite (Tuinstra et al., *J. Chemical Phys.* 53:1126-1130 (1970), which is hereby incorporated by reference in its entirety). The tape substrate was found to be composed of isotactic polypropylene, [—CH(CH$_3$)—CH$_2$—]$_n$ (Nielsen et al., *Polymer,* 43:2671-2676 (2002), which is hereby incorporated by reference in its entirety). The average spectra for the tape substrate, OGSR and IGSR training sets are plotted in FIG. 9 (red, blue and black traces, respectively). The averaged spectra illustrate the variations between the tape substrate and GSR particles, in which there are no common peaks.

Example 9

Chemical Mapping

After the training set was generated, tape lifting was performed to collect GSR samples from the cloth substrate of a discharge sample which was not previously characterized. Therefore, the samples were independent of the training set. Once a particle was located, an automated Raman mapping area was selected, which contained areas populated by both the tape substrate and GSR particle. The spot diameter of the excitation laser beam (approximately 1.7 µm) was smaller than typical GSR particles. It was determined that when the laser spot diameter fell within the boundaries of the particle, no spectral contribution from the substrate was collected. Only spectra collected at the boundaries of a GSR particle were found to be an exception to this rule.

Figure 10:
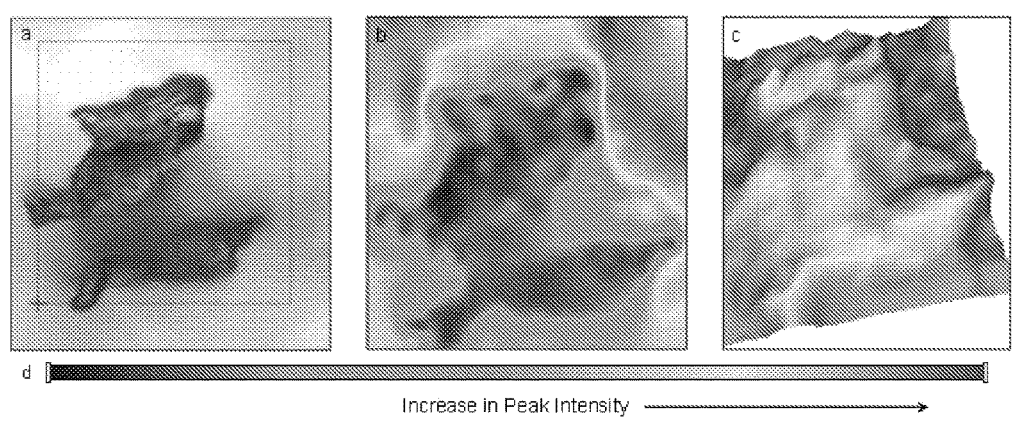
FIGS. 10a-d show the use of chemical mapping for OGSR detection.

FIG. 10*a* is an optical image of a mapped OGSR particle with an approximate diameter of 60 µm. 650 spectra were collected from this map. Using the integrated features in the OMNIC 8 software, chemical maps were generated from the Raman mapping data (FIG. 10*d* shows color scale corresponding to Raman peak intensity in the chemical maps). FIG. 10*b* illustrates the chemical map based on the Raman spectroscopic data in FIG. 10*a*. The color is based on the intensity of the Raman band at approximately 810 cm$^{-1}$. This vibrational mode is characteristic of isotactic polypropylene and is not observed in Raman data of GSR (Nielsen et al., *Polymer,* 43:2671-2676 (2002), which is hereby incorporated by reference in its entirety). Because the mapping spectra were baseline corrected and normalized before the generation of the image, a low spectral intensity at 810 cm$^{-1}$ is expected for spectra collected from OGSR. Low intensity (blue shading) correlates to the location of the OGSR, as compared to larger intensities (green, yellow and red shading) which are associated with the tape substrate. However, low Raman peak intensity at 810 cm$^{-1}$ is not an indication of GSR, as environmental contaminants may also give a low signal for this part of the spectrum. A much more specific approach is illustrated in FIG. 10*c*. FIG. 10*c* plots a three-dimensional profile of the chemical map, projecting the intensity of the Raman band at approximately 1288 cm$^{-1}$ in the z direction. This Raman band is inherent to nitrate ester explosives that are characteristic of OGSR, and not commonly found in the environment (Dalby et al., *J. of Forensic Sci.,* 55:924-943 (2010), which is hereby incorporated by reference in its entirety). The elevation in the z-direction of the particle (yellow and red shaded areas) relative to the flat tape substrate (green and blue areas) is clearly observable. Results illustrate that the Raman mapping approach is capable of plotting detected spectroscopic components in a three-dimensional space.

Example 10

Classification

Figure 9:
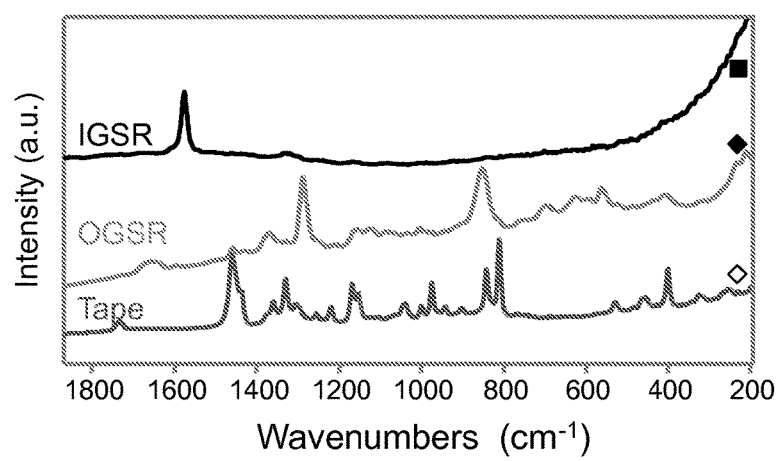
FIG. 9 shows mean training set spectra for IGSR, OGSR and the tape substrate (black (marked by ■), blue (marked by ♦), and red (marked by ◇) traces, respectively). The y-axis denotes spectral intensity in arbitrary units (a.u.). The mean spectra are easily differentiated by the naked eye.

The mean training set spectra illustrated in FIG. 9 are easily differentiated with the naked eye. Although these spectra are unique and descriptive for each analyte, they may not be indicative to individual spectra which could be collected from a GSR particle in a real world situation, when experimental spectra may vary in quality (i.e. signal to noise ratio). The identification of GSR based on visual inspections of Raman data for these questionable spectra, is not ideal for forensic purposes, as classifications may change between analysts. Furthermore, the visual inspection cannot account for the heterogeneity of GSR due to ammunition composition variations. We attempt to eliminate a degree of subjectivity in GSR detection by subjecting the experimental data to advanced statistics. This approach assigns unknown spectra as GSR without the need of an expert analyst's opinion and provides quantitative metrics for the strength of each classification.

The 650 mapping spectra were preprocessed as described above and were subjected to partial least square discriminant analysis (PLS-DA). This approach targeted the classification of unknown mapping spectra into the most probable of four classes (tape, OGSR, IGSR or unassigned). Any spectrum which received a score of <0.5 for each of the three groups, was classified as unassigned (Wise et al., PLS Toolbox 3.5 for Use with MATLAB™. Eigenvector Research, Inc., Manson (2004), which is hereby incorporated by reference in its entirety). The possibility of a spectrum to be unassigned signifies that the analysis did not simply force the spectra into the aforementioned groups. Rather than a simple differentiation, this analysis illustrates a true classification of unknown spectra. After the analysis was completed, the collection location of each spectrum was correlated via the montage image to the classified spectra. It was determined that the majority of the OGSR spectra that were misclassified as tape (false negative for GSR), were collected at the transition from the substrate to the particle. Conversely, spectra collected on the tape substrate one step from the GSR particle, were found to have high rates of false positive assignments as GSR. The misclassification of these boundary spectra is not alarming, as they occur due to the finite size of the laser beam spot, causing contributions from both the substrate and the particle to exist in these spectra. For practical forensic applications, boundary spectra collected from the tape substrate misassigned as GSR would not represent a true false positive result, as they would only occur if GSR was present.

Figure 11:
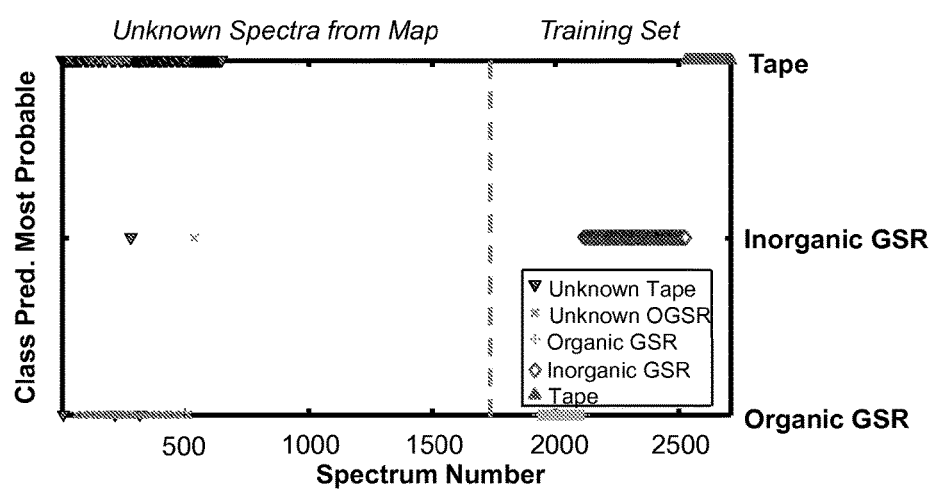
FIG. 11 shows PLS-DA classification scores plot treating the unknown Raman mapping spectra from FIG. 10a. X-axis represents a specific Raman spectrum. The y-axis is the most probable assignment of that spectrum as being OGSR, IGSR or tape. The training set spectra are plotted on the right side of the blue line. Training set spectra are represented by blue crosses (OGSR), white diamonds (IGSR) and grey triangles with red outlines (tape). The unknown mapping spectra are plotted on the left side of the blue line. Spectra collected over the OGSR particle are labeled with green X's, whilst purple triangles represent mapping spectra that were collected over the tape substrate.

104 "boundary spectra" were removed from the dataset. FIG. 11 is the resulting scores plot for the PLS-DA classification of the remaining spectra. Four latent variables (LVs) were used to describe the dataset. The x-axis plots a specific Raman spectrum, while the y-axis is the most probable assignment of that spectrum as tape, OGSR or IGSR. Spectra on the right side of the blue line represent training set spectra. Spectra labeled with blue crosses, white diamonds, and grey triangles with red shading were collected from OGSR, IGSR, and tape training set samples, respectively. Spectra on the left side of the blue line represent unknown mapping spectra from FIG. 10. Purple triangles represent spectra collected over the tape substrate whilst green X's were collected over the GSR particle. Results illustrate that zero of the training set spectra were misclassified. 164 of the 175 spectra collected from the inner portions of the OGSR particle, were correctly assigned (true positive for OGSR, scored on the bottom of the y-axis). Nine spectra were misclassified as tape and two as IGSR. Conversely, 367 of the 371 mapping spectra collected from tape were correctly assigned (true positive for tape). Zero mapping spectra were unassigned, thus all classifications had a probability of >0.5. Rates of true positives and negatives of 93.7% and 98.9%, respectively, were reported for assignment of OGSR mapping spectra.

Eight mapping experiments were performed using this procedure for both OGSR and IGSR particles, which were located on adhesive tape after the lifting procedure. Analyzed GSR particles ranged in size from 60 to 15 µm. Aggregate results classifying all mapping spectra (including boundary spectra) provided rates of true positives and negatives of 85.0% and 99.1% for OGSR and 90.4% and 92.9% IGSR, respectively. The classification rates are significantly increased when boundary spectra are ignored. It was determined that the average distance from the edge of a GSR particle to the first true positive spectral assignment as GSR, was calculated to be approximately 1.7 µm. Consequently, a GSR particle should be larger than 3.4 µm to be correctly identified by this method. This size detection limit is determined by the objective characteristics of the Raman microscope and could be adjusted respectively.

Raman spectroscopic mapping for GSR detection offers several advantages over current methodology. Raman mapping is nondestructive, rapid and not dependent upon detecting specific heavy metals which are not present in GSR originating from "green" ammunition. Statistical treatment of Raman mapping data eliminates a degree of bias during GSR detection, as the results are not dependent upon the opinion of an expert examiner. Furthermore, in the instance of a positive identification, results may be quantitated with confidence intervals and rates of true positives and negatives (sensitivity and specificity). When the method is fully developed, it has the potential to be a novel tool for the automated and rapid classification of unknown mapping spectra, for the purposes of identifying GSR for assisting with criminal forensic investigations. These classifications will be independent upon the opinions of an expert examiner.

The preliminary results reported here indicate the great potential of Raman microspectroscopy as an alternative method for GSR detection and identification. Nonetheless, additional validation studies should be performed to optimize the method and determine its accessibility for forensic purposes. The presence of environmental contaminants which often provide false positive assignments as GSR are known (Dalby et al., *J. of Forensic Sci.*, 55:924-943 (2010), which is hereby incorporated by reference in its entirety). Therefore, the next important step during method development would be the application of the combined Raman mapping and statistical approach, for the differentiation of GSR particles and environmental contaminants. Other factors that are under consideration by applicants include: quantifying the size limit of detection with various microscope objectives, establishing definitive assignments of vibrational modes and determining the analysis time as a function of the mapped area.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of detecting and distinguishing between inorganic and organic gunshot residue particles, said method comprising:
   providing a sample comprising gunshot residue;
   subjecting the sample to spectroscopic analysis to produce a spectroscopic signature for the sample;
   detecting the presence of inorganic gunshot residue particles based on the spectroscopic signature for the sample, wherein the inorganic gunshot residue particle has a size of 0.2 µm to 10 µm;
   detecting the presence of organic gunshot residue particles based on the spectroscopic signature for the sample, wherein the organic gunshot residue particle has a size of 10 µm to 1000 µm; and
   distinguishing between inorganic and organic gunshot residue particles based on the spectroscopic signature of the particles.

2. The method of claim 1, wherein the spectroscopic analysis is selected from the group consisting of Raman spectroscopy, vibrational spectroscopy, and combinations thereof.

3. The method of claim 2, wherein the spectroscopic analysis is vibrational spectroscopy and is selected from the group consisting of Infrared (IR) absorption, Fourier Transform Infrared absorption (FTIR), and Attenuated Total Reflection (ATR) FTIR.

4. The method of claim 3, wherein the spectroscopic analysis is Attenuated Total Reflectance (ATR) Fourier transform Infrared absorption (FTIR).

5. The method of claim 4, wherein the spectroscopic analysis is microscopic ATR FTIR.

6. The method of claim 2, wherein the spectroscopic analysis is Raman spectroscopy and is selected from the group consisting of NIR Raman spectroscopy and Surface Enhanced Raman spectroscopy (SERS).

7. The method of claim 1, wherein the spectroscopic signature is a multidimensional vibrational signature.

8. The method of claim 1 further comprising:
   determining, from the spectroscopic signature, the type of ammunition and/or the type of weapon used to fire the ammunition, from which the gunshot residue is derived.

9. The method of claim 8, wherein said determining identifies the type of ammunition.

10. The method of claim 9, wherein the type of ammunition is selected from the group consisting of 9 mm caliber, .45 caliber, .40 caliber, .22 caliber, and .38 Special.

11. The method of claim 8, wherein said determining identifies the type of weapon used to fire the ammunition.

12. The method of claim 8, wherein said determining comprises:
   comparing the spectroscopic signature for the sample to reference spectroscopic signatures for different types of ammunition and/or types of weapons used to fire the ammunition and
   characterizing the type of ammunition and/or the type of weapon used to fire the ammunition from the spectroscopic signature of the sample based on said comparing.

13. A method of detecting and distinguishing between inorganic and organic gunshot residue particles, said method comprising:

providing a sample comprising gunshot residue;

subjecting the sample to spectroscopic analysis to produce a spectroscopic signature for the sample, wherein the spectroscopic signature spans a range of wavenumbers;

creating one or more spectroscopic maps from the spectroscopic signature for the sample, wherein each different spectroscopic map is for a different wavenumber; and detecting the presence of and distinguishing between inorganic and organic gunshot residue particles based on the one or more spectroscopic maps for the sample, wherein the inorganic gunshot residue particle has a size of 0.2 µm to 10 µm, and wherein the organic gunshot residue particle has a size of 10 µm to 1000 µm.

14. The method of claim 13, wherein the one or more spectroscopic maps are multidimensional vibrational maps.

15. The method of claim 13, wherein spectroscopic maps are created for specific wavenumbers with the specific wavenumbers being markers for inorganic gunshot residue particles, organic gunshot residue particles, and/or tape substrate.

16. The method of claim 15, wherein the wavenumbers serving as a marker for inorganic gunshot residue particle include 1415 $cm^{-1}$.

17. The method of claim 15, wherein the wavenumbers serving as a marker for organic gunshot residue particle include 1646 $cm^{-1}$.

18. The method of claim 15, wherein the wavenumbers serving as a marker for tape substrate include 1728 $cm^{-1}$.

19. The method of claim 13, wherein the spectroscopic analysis is selected from the group consisting of Raman spectroscopy, vibrational spectroscopy, and combinations thereof.

20. The method of claim 19, wherein the spectroscopic analysis is vibrational spectroscopy and is selected from the group consisting of Infrared (IR) absorption, Fourier Transform Infrared absorption (FTIR), and Attenuated Total Reflection (ATR) FTIR.

21. The method of claim 20, wherein the spectroscopic analysis is Attenuated Total Reflectance (ATR) Fourier transform Infrared absorption (FTIR).

22. The method of claim 21, wherein the spectroscopic analysis is microscopic ATR FTIR.

23. The method of claim 19, wherein the spectroscopic analysis is Raman spectroscopy and is selected from the group consisting of NIR Raman spectroscopy and Surface Enhanced Raman spectroscopy (SERS).

24. The method of claim 13 further comprising:

determining, from the one or more spectroscopic maps, the type of ammunition and/or the type of weapon used to fire the ammunition from which the gunshot residue is derived.

25. The method of claim 24, wherein said determining identifies the type of ammunition.

26. The method of claim 25, wherein the type of ammunition is selected from the group consisting of 9 mm caliber, .45 caliber, .40 caliber, .22 caliber, and .38 Special.

27. The method of claim 24, wherein said determining identifies the type of weapon used to fire the ammunition.

28. The method of claim 24, wherein said determining comprises:

comparing the one or more spectroscopic maps for the sample to reference spectroscopic maps for different types of ammunition and/or types of weapons used to fire the ammunition and characterizing the type of ammunition and/or the type of weapon used to fire the ammunition from the one or more spectroscopic maps for the sample based on said comparing.

* * * * *

UNITED STATES PATENT AND TRADEMARK OFFICE
CERTIFICATE OF CORRECTION

PATENT NO. : 10,001,437 B2
APPLICATION NO. : 15/026529
DATED : June 19, 2018
INVENTOR(S) : Lednev It is certified that error appears in the above-identified patent and that said Letters Patent is hereby corrected as shown below:

In Claim 10, Column 22, Line 54, delete ".22 caliber" and insert --.22 L caliber-- in its place.

In Claim 26, Column 24, Line 23, delete ".22 caliber" and insert --.22 L caliber-- in its place.

Signed and Sealed this
Twenty-eighth Day of August, 2018

Andrei Iancu
*Director of the United States Patent and Trademark Office*